United States Patent
Bauer et al.

(10) Patent No.: US 9,795,688 B2
(45) Date of Patent: Oct. 24, 2017

(54) CELL-SPECIFIC TARGETING USING NANOSTRUCTURED DELIVERY SYSTEMS

(71) Applicant: SmartDyeLivery GmbH, Jena (DE)

(72) Inventors: Michael Bauer, Jena (DE); Ulrich Schubert, Jena (DE); Michael Gottschaldt, Jena (DE); Anja Trager, Trebgast (DE); Christian Pietsch, Jena (DE); Falk Gonnert, Jena (DE); Peter Recknagel, Albrechts (DE); Adrian Press, Jena (DE)

(73) Assignee: SMARTDYELIVERY GMBH, Jena (DE)

( * ) Notice: Subject to any disclaimer, the term of this patent is extended or adjusted under 35 U.S.C. 154(b) by 0 days.

(21) Appl. No.: 15/021,119

(22) PCT Filed: Sep. 11, 2014

(86) PCT No.: PCT/DE2014/000468
§ 371 (c)(1),
(2) Date: Mar. 10, 2016

(87) PCT Pub. No.: WO2015/035974
PCT Pub. Date: Mar. 19, 2015

(65) Prior Publication Data
US 2016/0220697 A1 Aug. 4, 2016

(30) Foreign Application Priority Data
Sep. 12, 2013 (EP) ..................................... 13184146

(51) Int. Cl.
*A61K 9/00* (2006.01)
*A61K 47/48* (2006.01)
(Continued)

(52) U.S. Cl.
CPC ........ *A61K 47/48884* (2013.01); *A61K 45/06* (2013.01); *A61K 47/48061* (2013.01);
(Continued)

(58) Field of Classification Search
CPC .................................................. A61K 47/48884
See application file for complete search history.

(56) References Cited

U.S. PATENT DOCUMENTS 6,692,934 B1 * 2/2004 Kirchgessner ......... C07K 14/47
435/320.1
2014/0369935 A1 * 12/2014 Okamoto ........... A61K 41/0057
424/9.6

FOREIGN PATENT DOCUMENTS

EP         2764861 A1      8/2014
JP   WO 2013051732 A1 *   4/2013  ........... A61K 1/0057
WO      2013/051732 A1    4/2013

OTHER PUBLICATIONS

Rungta, Selective Imaging and Killing of Cancer Cells with Protein-Activated Near-Infrared Fluorescing Nanoparticles, Macromolecular Bioscience, vol. 11, No. 7, 2011, 927-937.*

(Continued)

*Primary Examiner* — Paul Dickinson
(74) *Attorney, Agent, or Firm* — McDonnell Boehnen Hulbert & Berghoff LLP

(57) ABSTRACT

The invention relates to a nanostructured delivery system comprising at least one polymer and/or at least one lipid and at least one polymethine dye, wherein the at least one polymethine dye acting as a targeting unit brings about the targeted transport of the nanostructured delivery system into a target issue. The invention also relates to a pharmaceutical composition and the uses of the nanostructured delivery system for transporting said system and, optionally, a pharmaceutical active ingredient into the target tissue, as well for treating liver and/or kidney diseases.

15 Claims, 14 Drawing Sheets

Figure 3:
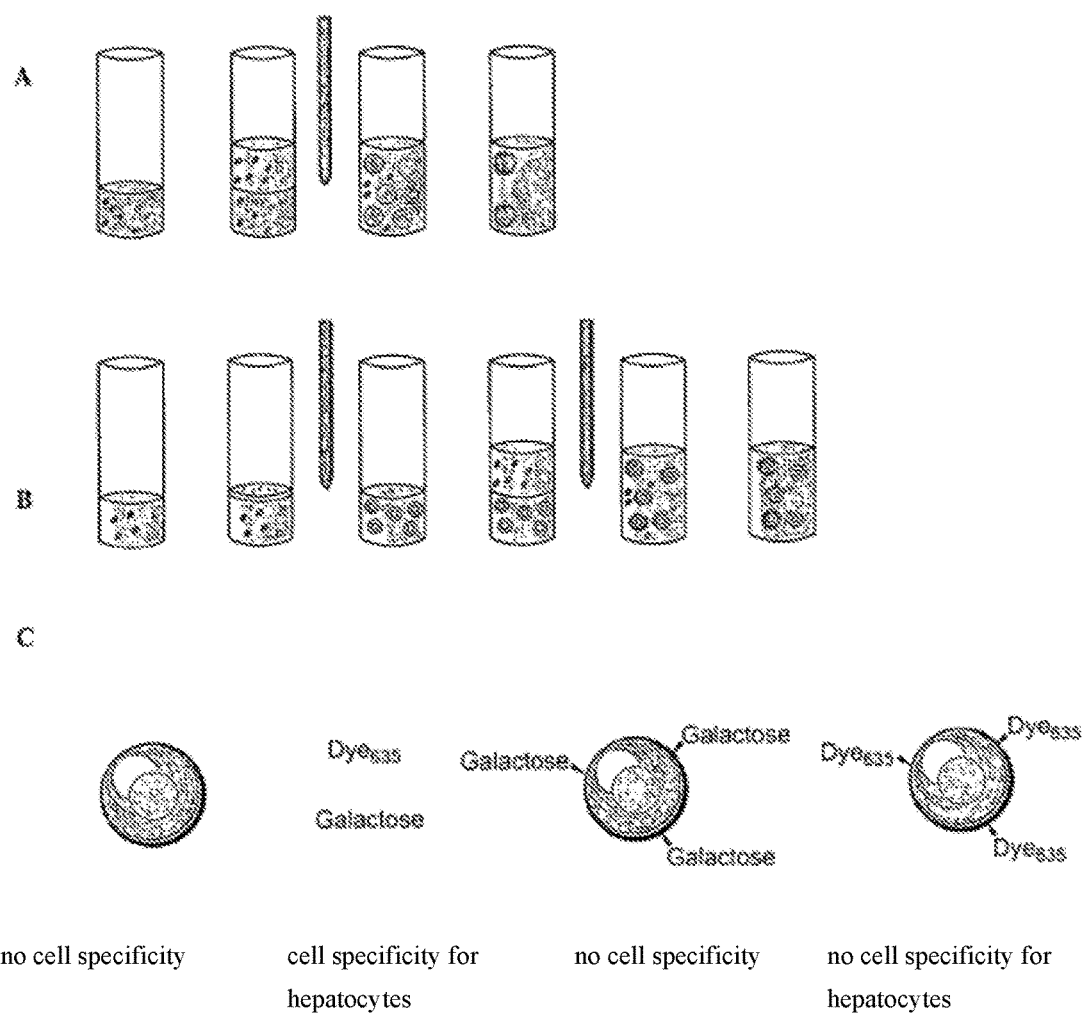

(51) Int. Cl.
   *A61K 49/00*   (2006.01)
   *A61K 45/06*   (2006.01)
   *C12N 15/113*  (2010.01)

(52) U.S. Cl.
   CPC .. *A61K 47/48815* (2013.01); *A61K 47/48907* (2013.01); *A61K 47/48915* (2013.01); *A61K 49/0032* (2013.01); *A61K 49/0084* (2013.01); *A61K 49/0093* (2013.01); *C12N 15/1137* (2013.01); *C12N 2310/14* (2013.01); *C12N 2320/32* (2013.01)

(56) References Cited

OTHER PUBLICATIONS

Noh, Near-Infrared Emitting Polymer Nanogels for Efficient Sentinel Lymph Node Mapping, ACS Nano, vol. 6, No. 12, 2012, 7820-7831.*

European Search Report for EP13184146, mailed Jan. 23, 2014.
Jiang, et al., "Targeted gene silencing of TLR4 using liposomal nanoparticles for preventing liver ischemia reperfusion Injury," American Journal of Transplantation, 11(9): 1835-1844, Jul. 2011.
Jin, et al., "Improved therapeutic effect of DOX-PLGA-PEG micelles decorated with bivalent fragment HAb18 F(ab')2 for hepatocellular carcinoma," Biomacromolecules, 11: 2422-2431, 2010.
Yeh, et al., "Tumor targeting and MR imaging with lipophilic cyanine-mediated near-infrared responsive porous GD silicate nanoparticles," Biomaterials, 34(22): 5677-5688, Apr. 2013.
International Search Report for PCT/DE2014/000468, mailed Jan. 22, 2015.
Noh, et al., "Near-Infrared Emitting Polymer Nanogels for Efficient Sentinel Lymph Node Mapping," ACS NANO, 6(9):7820-7831, Sep. 2012.
Rungta, et al., "Selective imaging and killing of cancer cells with protein-activated Near-infrared Fluorescing nanoparticles," Macrmolecular Bioscience, 11(7): 927-937, Apr. 2011.

* cited by examiner

Table 1

| Variation | Effect on nanoparticle (constituents) | Result |
|---|---|---|
| Replacement of DY | Altered charge of the NP and functionalization | Different target tissue, different target cell, changes in transport efficiency |
| Change in degree of substitution of a DY | Change in the hydrophilic and/or lipophilic character | Renal/hepatic specificity of the dye/particle |
| Change in the number of central conjugated double bonds in the DY | Shift in the emission and absorption spectrum | Adjustment of detectability, simultaneous detection of multiple DYs at the same time |
| Change in the shell polymer | Altered endosomal and/or intracellular stability of the nanoparticle, altered encapsulation efficiency | Control of the release rate and amount of active ingredient transported in the nanoparticle |
| Change in the active ingredient transported | Possible change in encapsulation efficiency, in the hydrophobic/hydrophilic equilibrium of the particle | Altered effect in the target organ |
| Change in the preparation of the nanoparticles | Size check, surface groups may be varied | Passive uptake and accumulation in organs and/or cells as assistance for active targeting |
| Change in the nanoparticle stabilizers | Altered stability in the production, charge and size of the particles | Altered uptake and rate of release |

DY = polymethine dye
NP = nanoparticle

Figure 1

A
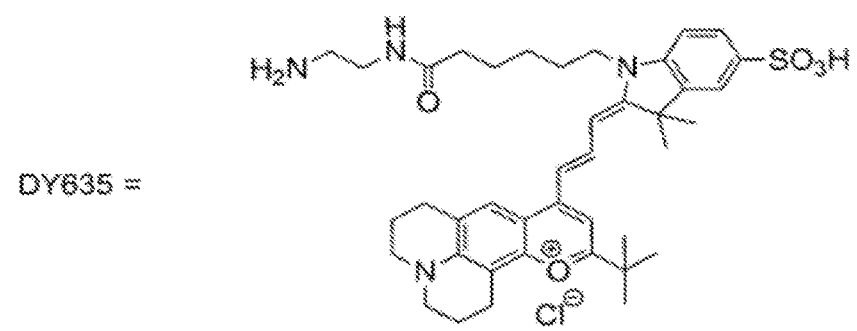
B
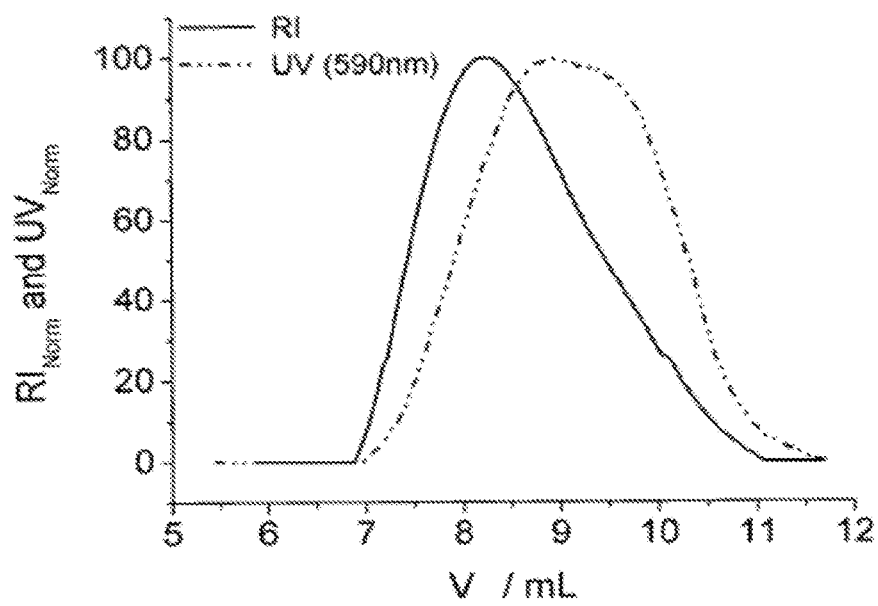
Figure 2

** Significance level 0.99; p each < 0.0025, U test

Table 2:

| General structure Hepatocyte-targeting unit: | General structure Renal parenchyma cell-targeting unit: |
|---|---|
| Structures I-IV with $R^{13} = SO_3^-$ (or $SO_3H$), and with $R^{17}$ = linker to polymer 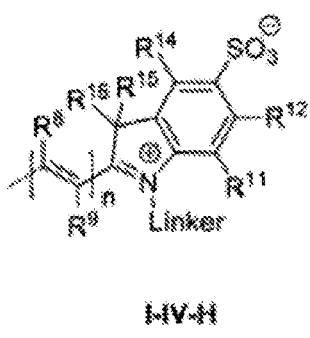 I-IV-H | Structures I-IV with $R^{13} = SO_3^-$ (or $SO_3H$), $R^{15}$ or $R^{16}$ = linker to polymer and $R^{17} = (CH_2)_a\text{-}SO_3^-$ where a is 1-18 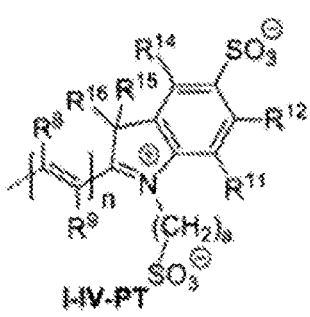 I-IV-PT |
| Exemplary structures for hepatocyte targeting: | Exemplary structures for targeting renal parenchyma cells (mainly proximal tubulus cells) |
| DY-680 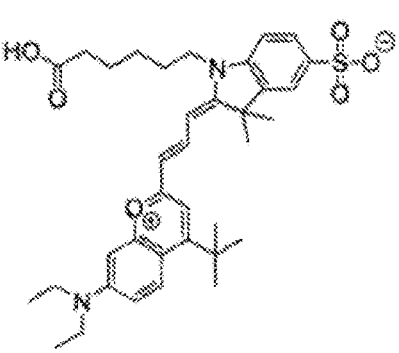 | DY-778 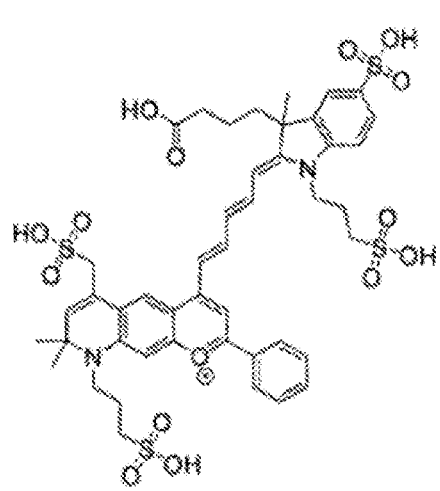 |

Figure 8

CELL-SPECIFIC TARGETING USING NANOSTRUCTURED DELIVERY SYSTEMS

CROSS-REFERENCE TO RELATED APPLICATION

This application is a U.S. national phase of International Application No. PCT/DE2014/000468, filed Sep. 11, 2014, which claims priority to European Patent Application No. 13184146.2, filed Sep. 12, 2013 the disclosure of which are hereby incorporated by reference in their entireties.

The present invention relates to nanostructured delivery systems comprising one or more polymers and/or lipids as well as one or more targeting units, in particular polymethine dyes for targeted transport of the nanostructured delivery system into a target tissue. The invention also relates to target-specific transport of one or more active pharmaceutical ingredients into a specific target tissue (cell-specific targeting) and use of the nanostructured delivery system according to the invention for prevention and/or treatment of diseases.

In the prior art the use of nanoparticles with couple dyes in clinical diagnostics is known for detection of organ functions or protein expressions in diagnosing pathogenic states, for example, or for proteomic analyses, where the coupled dyes, usually fluorescent dyes such as cyanines, are used as markers whose fluorescence and absorption properties are measured.

WO2012/013247A1 describes the use of polymethine fluorescent dyes for determining an organ function, in particular the function of liver or kidneys, wherein the dye is used as a marker in a tissue or a body fluid, such as blood or urine and is radioactively energized, and then the fluorescence emission of the dye is detected, the data is detected and analyzed to determine the organ function being determined.

In WO2010/116209A1 it is reported that a clinical condition based on abnormal secretion of selectin.

In addition, the use of nanoparticles that transport active ingredients into a certain tissue in a targeted manner is also known in the prior art (C. Sheridan, *Proof of concept for next-generation nanoparticle drugs in humans*. Nat Biotechnol, 2012 30(6): pp. 471-3; S. E. Gratton et al., *The effect of particle design on cellular internalization pathways*. Proc Natl Acad Sci USA, 2008 105 (33): pp. 11613-8).

Targeted or cell-specific transport of an active ingredient, also known as "drug targeting" or "targeted drug delivery," is understood to refer to the targeted and selective accumulation and release of an active ingredient at a desired site of action, wherein the efficacy in the action of the active ingredient is increased and the systemic side effects for the surrounding tissue are reduced. Active ingredients that are transported often include antibodies, peptides or small molecules, such as oligonucleotides or nucleic acids.

The active ingredient transporting nanoparticles known in the prior art are used in tumor therapy and function according to the following mechanisms: the nanoparticle is provided with either a shell layer or an antibody. If the nanoparticle is coated with an aqueous shell layer, it is rendered unidentifiable for the immune system. If this nanoparticle is injected and is not attacked by the immune system, it diffuses through the fenestrated blood vessels, which are "leaky" in the tumor and have significantly larger orifices (fenestrations) in comparison with normal blood vessels and is absorbed by the surrounding cells which also have an increased permeability in comparison with healthy cells. The disadvantage is that not only do the desired cells take up the nanoparticle but also other (healthy cells) to which the nanoparticle is transported nonspecifically through the blood vessels. This can lead to serious adverse effects. Another disadvantage is that this transport is limited to tumor tissue, i.e., there cannot be any transport into any other tissue such as the liver or kidneys. This transport takes place in a passive manner and the uptake is nonspecific, i.e., nonselective. In the second method, the nanoparticle is provided with antibodies on its surface after being synthesized. These constructs target cells with antigens to which these antibodies bind. This transport mechanism is also passive and nonselective.

These processes of passive enrichment of nanoparticles, liposomes or macromolecules described above is referred to as the EPR effect ("enhanced permeability and retention") and is a passive drug targeting. As already mentioned, the advantages include the fact that these transport processes are not active and are not selective.

Nowhere in the prior art is a description of an active and selective transport and/or delivery system whose active transport takes place selectively into a specific target tissue by means of special targeting units and with which (pharmaceutical) active ingredients can be transported at the same time into the target tissue ("drug targeting"; cell-specific targeting) and accumulation of the delivery system and optionally the (pharmaceutical) active ingredient in the target tissue by way of the targeting unit is not only achieved but can also be tracked and verified.

There is therefore a demand for providing an improved transport and/or delivery system that will trigger active and selective transport of delivery systems and active ingredients into a target tissue. There is also a demand for using such a transport and/or delivery system for the transport of active pharmaceutical ingredients in the treatment of diseases.

Such a transport system is made available with the present invention. The present invention relates to a unique theragnostic system that can be combined in a variety of ways to actively and selectively transport various active pharmaceutical ingredients (for example, hydrophilic, lipophilic, hydrophobic, amphiphilic, anionic and cationic substances) into a target tissue (targeted or cell-specific transport of active ingredient or "drug targeting").

In its first subject matter, the present invention relates to a nanostructured delivery system, comprising at least one polymer and/or at least one lipid and at least one polymethine dye, wherein the at least one polymethine dye acting as a targeting unit triggers the targeted transport of the nanostructured delivery system into a target tissue.

If the nanostructured delivery system according to the invention comprises polymers, it is referred to herein as "nanoparticles"; if it comprises lipids it is referred to herein as a "liposome." If the nanostructured delivery system according to the invention comprises both polymers and lipids, it is referred to herein as "nanoparticle" or as "liposome." Accordingly, the terms "nanoparticle" and "liposome" are used synonymously according to the invention and also relate to a nanostructured delivery system comprising both polymers and lipids.

Nanoparticles are structures which are smaller than 1 μm in size and may be constructed of a plurality of molecules. They are characterized in general by a higher ratio of surface to volume and thus offer a greater chemical reactivity. These nanoparticles may consist of polymers wherein these polymers are characterized by the fact that certain units (monomers) are repeating units. The polymers are covalently bonded to one another by the chemical reaction of these monomers (polymerization). If some of these polymers have hydrophobic properties, they may form nanoscale structures (e.g., nanoparticles, micelles, vesicles) in an aqueous environment. Due to their hydrophobic properties, lipids may also be used to form nanoparticles (micelles, liposomes).

A preferred embodiment of the present invention relates to a nanostructured delivery system, wherein the at least one polymer is selected from the group consisting of polyesters, poly(meth)acrylates, polystyrene derivatives, polyamides, polyurethanes, polyacrylonitriles, polytetrafluoroethylenes, silicones, polyethylene glycols, polyethylene oxides and polyoxazolines and their copolymers, preferably in a variety of compositions such as random, gradient, alternating, block, graft or star copolymers, or the at least one lipid is selected from the group consisting of saturated and unsaturated fatty acids, preferably cholesterol, palm ethyl acid, phospholipids, sphingolipids and glycolipids. The polymer and/or lipid according to the invention is/are preferably a biocompatible polymer and/or lipid.

The polymer according to the invention is especially preferably a hydrophobic, hydrophilic, amphiphilic, anionic and/or cationic polymer. The polymer is in particular preferably selected from the group consisting of PLGA, PLA, PCL, PGA, PDMAEMA, PMMA, PMAA, PEI, PEtOx, PEG.

Substances that actively and selectively trigger the transport of the nanostructured delivery system according to the invention into a specific target tissue are referred to as a "targeting unit" in the sense of this invention. Targeting units according to the invention are polymethine dyes. The terms "targeting unit" and "polymethine dye" are used synonymously according to this invention. As already described above, polymethine dyes are used in the prior art as substances that serve as markers for determining a physiological condition, for example, an organ function or as proof or detectors for the accumulation of a certain substance, molecule or chemical construct such as a nanoparticle in a tissue. The mechanism of action of polymethine dyes known in the prior art, such as, for example, indocyanine green (ICG), IRDye800, is by no means the mediation of any cell-specific uptake but instead is the use as a "marker" or "label" or as a "photosensitizer" and in the case of ICG as a nonspecific cyanine dye. Nowhere in the prior art is the effect of polymethine dyes as a targeting unit described or even indicated, i.e., as a substance capable of actively, selectively and in a targeted manner transporting other substances such as nanoparticles in general or an nanostructured delivery system according to the invention as in this case, into a specific target tissue. This is a different novel and technical effect of polymethine dyes as targeting units according to the invention of which those skilled in the art were not aware. Due to the fact that polymethine dyes have uniform characteristic chemical properties and structures, polymethine dyes can be used as targeting units in the sense of this invention in the entire range claimed according to the invention.

A preferred embodiment of the present invention relates to a nanostructured delivery system wherein the at least one polymethine dye is a symmetrical or asymmetrical polymethine of general structure I, II, III or IV:

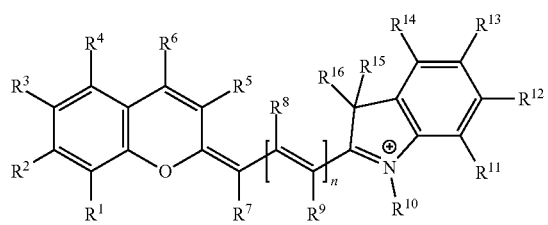

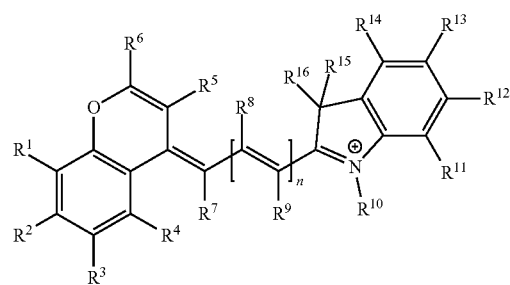

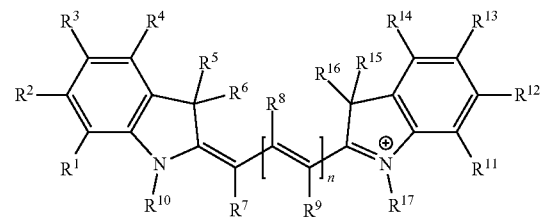

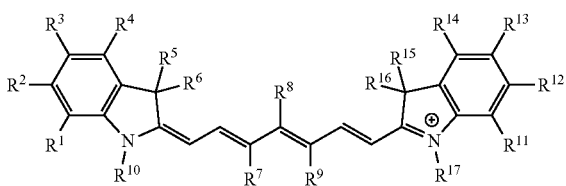

where
a. n stands for the numerical values 0, 1, 2, 3, 4, 5, 6, 7, 8, 9 or 10,
b. $R^1$-$R^{17}$ may be the same or different and may be hydrogen, one or more alkyl, tert-alkyl, cycloalkyl- (the "alkyl" and "cycloalkyl" radicals also include olefinic structures) or aryl, carboxyaryl, dicarboxyaryl, heteroaryl or heterocycloaliphatic radicals, alkyloxy, alkylmercapto, arlyoxy, arylmercapto, heteroaryloxy, heteroarylmercapto groups, a hydroxyl, nitro or cyano group, an alkyl-substituted or cyclic amine function and/or two ortho-position radicals, e.g., $R^3$ and $R^4$, $R^{13}$ and $R^{14}$ and/or $R^1$ and $R^2$ and $R^{11}$ and $R^{12}$ and/or $R^7$ and $R^9$ together may form an additional aromatic, heteroaromatic, aliphatic or heteroaliphatic ring,
c. at least one of the $R^1$-$R^{17}$ substituents has a solubilizing and/or ionizable or ionized substituent such as $SO_3^-$, ($-SO_3H$), $PO_3^{2-}$, COOH, OH or $NR_3^+$, cyclodextrins or sugar, which determines the hydrophilic properties of these polymethine dyes, wherein this substituent may also be bound to the polymethine dye by a spacer group, and
d. at least one of the $R^1$-$R^{17}$ substituents has a reactive group (linker) such as isocyanates, isothiocyanates, hydrazines, amines, mono- and dichloro- or mono- and dibromotriazines, aziridines, epoxies, sulfonyl halides, acid halides, carboxylic anhydrides, N-hydroxysuccinimide esters, imido esters, carboxylic acids, glyoxal, aldehyde, maleimide or iodacetamide and phosphoramidite derivatives or azides, alkynes or olefins, wherein this substituent may also be bound to the polymethine dye by a spacer group, e. the aromatic, heteroaromatic, aliphatic or heteroaliphatic spacer group consists of structural elements such as $[(CH_2)_a-Y-(CH_2)_b]_c$ or $[(C_6H_4)_a-Y-(C_6H_4)_b]$, where Y may be the same or different and comprises $CR_2-$, $O-$, $S-$, $SO_2$, $SO_2NH-$, $NR-$, $COO-$ or $CONR$ functions, wherein it is bound to one of the $R^1$-$R^{17}$ substituents, and a and b may be the same or different and have numerical values of 0-18 and numerical values for c of 0-18, f. the $R^8$ and $R^9$ substituents with corresponding n=2, 3, 4 or 5, may also be present 2×, 3×, 4× or 5×, and these may be the same or different.

According to the invention, the terms "targeting unit" and "polymethine dye" are used synonymously.

The targeting units (polymethine dyes) are conjugated by a linker to the polymer:
general structure polymer-linker-targeting unit:
polymer^linker^targeting unit The general structure of a linker according to the invention can be described as follows: at least one structural unit (polymer and/or targeting unit) has a reactive group (linker), such as isocyanates, isothiocyanates, hydrazines, amines, mono- and dichloro- or mono- and dibromotriazines, aziridines, epoxies, sulfonyl halides, acid halides, carboxylic anhydrides, N-hydroxysuccinimide esters, imido esters, carboxylic acids, glyoxal, aldehyde, maleimide or iodacetamide and phosphoramidite derivatives or azides, alkynes or olefins, wherein these substituents may also be bound to the polymethine dye and/or to the polymer by a spacer group. The targeting unit is linked to the polymer (or vice versa) by a covalent bond by means of these reactive groups.

The chemical bonds between the polymer and/or the targeting unit and the linker may be selected to be biostable or biodegradable. One or more different targeting units may be bound to a polymer. Likewise polymers provided with various targeting units can be combined in a nanoparticle. Thus the polymer and the targeting unit or even both may be different. Instead of a polymer, a lipid may also be used under the same conditions as those described above, and a liposome may be used accordingly instead of a nanoparticle.

In a preferred embodiment of the present invention, the at least one polymethine dye of the nanostructured delivery system is a DY dye, preferably selected from the group consisting of DY-635, DY-680, DY-780, DY-880, DY-735, DY-835, DY-830, DY-730, DY-750, DY-850, DY-778, DY-878, DY-704, DY-804, DY-754, DY-854, DY-700, DY-800, ICG and DY-IRDYE 800CW. In addition, the polymethine dyes DY-630, DY-631, DY-632, DY-633, DY-634, DY-636, DY-647, DY-648, DY-649, DY-659, DY-651, DY-652, DY-590, DY-548, DY-495 and DY-405 are also preferred. These include polymethine dyes as targeting units, which trigger a selective transport into hepatocytes or renal parenchyma cells. The general structures of a hepatocyte targeting unit according to the invention as well as a parenchyma cell targeting unit according to the invention and also the corresponding examples are given in Table 2 in FIG. 8. These targeting units are selective for a cell type (hepatocyte or renal parenchyma cells) and can transfer this cell selectivity to a nanoparticle or a liposome when they are bound to the latter by a chemical bond. The selectivity of the targeting unit occurs here due to the interaction with the influx transporters, which are expressed by the target cells. The targeted units also have fluorescent properties in the red to infrared range. These fluorescent properties can also be transferred to the nanostructured delivery system, more specifically to the nanoparticle or the liposome, so that not only is it possible to detect the accumulation of dye but also (when bound to the nanoparticle and/or to the liposome) accumulation of the nanoparticle and/or of the liposome in blood and in tissue can also be detected.

As targeting units, the polymethine dyes according to the invention transport the nanostructured delivery system selectively into the target tissue. The selectivity is crucial for successful transport into the "correct" tissue and only into said tissue and constitutes a very great advantage in comparison with the prior art. The polymethine dyes serve as transporter ligands for tissue-specific transporters. In a preferred embodiment, the at least one polymethine dye serves as a transporter ligand for the at least one tissue-specific transporter. The following properties are important in order for a polymethine dye to be suitable as such a transporter ligand: (1) the hydrophobicity and (2) the combination with the specific structure. These properties are crucial for being recognized as a ligand (selectivity of the dye) by a tissue-specific transporter.

If the polymethine dye is bound to a polymer or lipid, so that it is exported outward after synthesis of the nanoparticle or of the liposome, it transfers its selectivity to the nanoparticle and/or the liposome. The following processes, which are crucial for the selectivity of the nanoparticle and/or the liposome, then occur after systemic administration or topical application:

The nanoparticle or liposome with the (at least one) exposed polymethine dye flows past various tissues.

The polymethine dye is detected by the tissue-specific basolateral or apical influx transporters, based on its hydrophobicity and structure, and interacts with them at the cell surface.

The interaction of the polymethine dye with the influx transporter does not lead to direct transport of the entire nanostructured delivery system or the nanoparticle or the liposome through this transporter, because this nanoparticle or liposome with the covalent and stable bond is too large.

The accumulation and immobilization of the nanoparticle or liposome on the cell surface increases the interaction between the cell membrane and nanoparticle or liposome so that there is a cellular uptake (endocytosis) of the nanoparticle or liposome.

A preferred embodiment of the invention relates to a nanostructured delivery system, wherein the at least one polymethine dye is detected by the at least one tissue-specific transporter and interacts with this at the cell surface of the cells of the target tissue so that the nanostructured delivery system preferably accumulates at the cell surface and is immobilized there and preferably taken up into the cells of the target tissue.

The cell selectivity is obtained through the specific interaction of the polymethine dye, which is coupled to the nanoparticle or the liposome and is detected by the corresponding tissue-specific influx transporter. Influx transporters for the polymethine dyes according to the invention have been defined for hepatocytes and renal parenchyma cells.

Polymethine dyes according to the invention, which are taken up specifically by influx transporters of the basolateral membrane of hepatocytes, make the nanoparticle specific for hepatocytes. According to current information and the FDA, the following fall under the influx transporters of hepatocytes:

| Name | Gen |
|---|---|
| OATP1B1, OATP-C, OATP2, LST-1 | SLCO1B1 |
| OATP1B3, OATP8 | SLCO1B3 |
| OATP2B1 | SLCO2B1 |
| OATP1A2 | SLCO1A2 |
| NaDC3, SDCT2 | SLC13A3 |
| NTCP | SLC10A1 |
| OCT1 | SLC22A1 |
| OCT3 | SLC22A3 |
| OAT2 | SLC22A7 |
| OAT1 | SLC22A6 |
| OAT3 | SLC22A8 |
| PGT | SLCO2A1 |

Ligands of these transporters comprise in particular all polymethine dyes having a structure such as that shown in Table 2 (FIGS. 8a-e), left column.

Polymethine dyes according to the invention that are taken up specifically by influx transporters of the basolateral membrane of renal parenchyma cells (mainly proximal tubular cells) make the nanoparticle specific for these types of cells. According to the current information and the FDA, the following fall under the influx transporters of the renal parenchyma cells (mainly proximal tubular cells):

| Name | Gen |
|---|---|
| OCT2 | SLCO1B1 |
| OAT1 | SLCO1B3 |
| OAT3 | SLC22A8 |
| OATP4A1 | SLCO4A1 |
| OATP4C1 | SLCO4C1 |
| OCT1 | SLC22A1 |
| OCT3 | SLC22A3 |
| PGT | SLCO2A1 |

Ligands in these transporters comprise in particular all the polymethine dyes having a structure such as that shown in Table 2 (FIGS. 8a-e), right column.

One embodiment of the invention that is still preferred thus relates to a nanostructured delivery system, wherein the at least one polymethine dye triggers the uptake of the nanostructured delivery system into the cells of the target tissue by means of at least one tissue-specific transporter. The tissue-specific transporter is especially preferably selected from the group consisting of OATP1B1, OATP-C, OATP2, LST-1, OATP1B3, OATP8, OATP2B1, OATP1A2, NaDC3, SDCT2, NTCP, OCT1, OCT3, OAT2, OAT1, OAT3, PGT, OCT2, OAT1, OATP4A1, OATP4C1.

The terms "tissue-specific transporter," "transporter" and "influx transporter" are used synonymously according to the invention.

The terms "nanostructured delivery system," "nanoparticle" and "liposome" are used according to the invention in conjunction with the transport to and uptake into the target tissue by means of a tissue-specific transporter.

After uptake of the nanostructured delivery system and/or the nanoparticle or the liposome into the target tissue, the polymethine dye is released and an active pharmaceutical ingredient optionally also covered by the present invention is also released.

Release of a nanoparticle as an ingredient of the nanostructured delivery system:

1. acidification of the endosome→destabilization of the nanoparticle, degradation of the polymer by spontaneous or enzymatic cleavage;
2. release of active substances (that are capable of penetrating the endosome);
3. release of the active ingredient, desorption of the dye from the polymer;
4. polymer constituents are supplied for various metabolic pathways, dye is secreted.

Release of a liposome as an ingredient of the nanostructured delivery system:

1. uptake by endosomes→acidification→fusion of the liposome with the endosome membrane after endocytosis or direct fusion of the liposome with the cell membrane;
2. both pathways result in direct release of the active ingredient into the cytoplasma;
3. if the targeting unit (polymethine dye) is bound to the lipid by a biolabile bond, this bond can be cleaved and the lipid is excreted.

When using a biostable bond, the polymethine dye remains bound to the lipid. If there is subsequently degradation of the lipid, the polymethine dye may be secreted with a small lipid radical. It is probable that a portion of the lipid can be incorporated with the polymethine dye into the cell membranes.

Another particularly preferred embodiment of the present invention relates to a nanostructured delivery system, wherein the nanostructured delivery system additionally comprises at least one active pharmaceutical ingredient. The at least one active pharmaceutical ingredient is preferably selected from the group consisting of low-molecular substances, in particular inhibitors, inductors or contrast agents as well as higher molecular substances, in particular potentially therapeutically usable nucleic acids (e.g., short interferon RNA, short hairpin RNA, micro RNA, plasmid DNA) and proteins (e.g., antibodies, interferons, cytokines). The following table describes examples of active ingredients whose specific administration via the nanostructured delivery system of the present invention permits novel therapeutic options:

| Active Ingredient | Examples of active ingredient | Treatment/ Disease | Organ/ Tissue |
|---|---|---|---|
| Glucocorticoids | decortin | organ transplants | liver, kidneys |
| Cytostatics, e.g., alkylating agents | cyclophosphamide | organ, transplants tumors | liver, kidneys |
| Antimetabolites | methotrexate | organ transplants, tumors | liver, kidneys |
| Intercalating agents | mitoxantrone | organ transplants, tumors | liver, kidneys |
| Antibodies | Rituximab (anti-CD20), daclizumab (anti-CD25) | organ transplants, tumors | liver, kidneys |
| Interferons | IFN-β, IFN-γ | organ transplants | liver, kidneys |
| Phosphoinositol-3 kinase inhibitors | D-116883, AS605240, IPI-145 | tumors, sepsis | liver, kidneys |
| Coxibs | celecoxib, etoricoxib | acute renal failure | kidneys |
| JNK inhibitors | CC-401, celgene | Malaria | liver |
| X-ray contrast agents | peritrast | diagnosis of tumors, for example | liver, kidneys |

-continued

| Active Ingredient | Examples of active ingredient | Treatment/ Disease | Organ/ Tissue |
|---|---|---|---|
| Paramagnetic X-ray contrast media | gadopentetate-dimeglumine (magnevist) | diagnosis of tumors, for example | liver, kidneys |

The active pharmaceutical ingredient is particularly preferably a lipophilic, hydrophobic, hydrophilic, amphiphilic, anionic and/or cationic active pharmaceutical ingredient.

The term "active pharmaceutical ingredient" is understood according to the invention to refer to any organic or inorganic molecule, substance or compound having a pharmacologic effect. The term "active pharmaceutical ingredient" is used synonymously herein with the terms "drug" and "medication."

The nanostructured delivery system according to the present invention is a theragnostic system that is unique so far and can be combined a variety of ways to transport a wide variety of substances, in particular active pharmaceutical ingredients (e.g., or lipophilic small molecules, but also nucleic acids) actively and selectively into a specific target tissue. The transport of the active pharmaceutical ingredient is triggered by targeting units, polymethine dyes as a component of the nanostructured delivery system interacting with tissue-specific transporters on the target cell. Through the choice of the polymethine dyes (DY), the active pharmaceutical ingredients and the polymers and/or lipids as well as the variation in their parameters, it is possible to produce the nanoparticle and/or liposomes which are tailored individually to the respective application, in particular the active pharmaceutical ingredient to be transported and/or the target tissue. It is possible in this way to efficiently transport one or more active pharmaceutical ingredients as components of the nanostructured delivery system into a specific tissue or cell type (target tissue) and release them there. The active pharmaceutical ingredients may comprise those having little or no bioavailability without being enclosed in a nanoparticle or a liposome or having little or no stability in vivo or being able to act only in specific organs and/or cells (target tissue). The specificity and accumulation of the nanostructured delivery system (nanoparticle or liposome) and/or components thereof such as polymers, lipids or active pharmaceutical ingredient(s) in the target tissue can be verified and tracked, i.e., detected by means of the fluorescence properties in the red to infrared range of the nontoxic polymethine dyes.

The "target tissue" in the sense of the present invention includes all tissues, organs or cells in which the transport of the nanostructured delivery system and/or components thereof, in particular an active pharmaceutical ingredient, is possible and reasonable. Target tissues include in particular all tissues, organs or cells into which transport of one or more active pharmaceutical ingredients is possible and reasonable, for example, for treatment or diagnosis of a disease. Examples of target tissues preferred according to the invention include but are not limited to the liver, kidneys and tumors, in particular those originating in these tissues, for example, hepatocellular carcinomas or hypernephromas. The terms "target tissue," "target cell," "cells of a target tissue" and "organ" are used synonymously in this context.

Due to the conjugation of the polymethine dyes according to the invention (hereinafter DY) on polymers or lipids, functionalized polymers (e.g., DY-PLGA, DY-PLA, DY-PCL) and/or functionalized lipids are produced. Next these are used for producing nanoparticles and/or liposomes, preferably by means of a single or double emulsion technique or precipitation technique. It is possible here to tailor the nanoparticles and/or liposomes individually to the respective situation. The various possibilities are listed as examples in Table 1 (FIG. 1). The polymethine dyes can be conjugated with a variety of different polymers and/or lipids, so that through the special combination of polymethine dye with a lipid or polymer, highly selective nanostructured delivery systems can be provided. Synthesis of functionalized polymers is diagrammed schematically in FIG. 2 and is illustrated in detail in Example 1. The production of functionalized polymers or lipids, nanoparticles and liposomes according to the invention as well as the inclusion of active pharmaceutical ingredients can be performed according to traditional methods known from the prior art. Preferred production processes are disclosed in the examples and figures in the present invention.

Another subject matter of the invention relates to a pharmaceutical composition containing a nanostructured delivery system according to the invention as well as suitable excipients and additives.

The "excipients and additives" according to the invention are understood to include any pharmacologically acceptable and therapeutically expedient substance that is not an active pharmaceutical ingredient but can be formulated together with the active pharmaceutical ingredient in the pharmaceutical composition in order to influence qualitative properties of the pharmaceutical composition, in particular to improve them. The additives and/or excipients preferably do not have any mentionable adverse pharmacological effect or they at least do not have any adverse pharmacological effect with regard to the intended treatment. Suitable excipients and additives include, for example, pharmaceutically acceptable organic or inorganic acids, bases, salts and/or buffer substances. Examples of inorganic acids include hydrochloric acid, hydrobromic acid, nitric acid, sulfuric acid and phosphoric acid wherein hydrochloric acid and sulfuric acid in particular are preferred. Examples of suitable organic acids include malic acid, tartaric acid, maleic acid, succinic acid, acetic acid, formic acid and propionic acid and in particular preferably ascorbic acid, fumaric acid and citric acid. Examples of pharmaceutically acceptable bases include alkali hydroxides, alkali carbonates and alkali ions, preferably sodium. Mixtures of these substances may be used in particular to adjust and buffer the pH. Preferred buffer substances in the sense of the invention also include PBS, HEPES, TRIS, MOPS, as well as other physiologically acceptable buffer substances. Additional suitable excipients and additives include solubilizers or diluents, stabilizers, suspension mediators, preservers, fillers and/or binders as well as other conventional excipients and additives known in the prior art. The choice of excipients as well as the quantities thereof to be used will depend on the active pharmaceutical ingredient and how it is administered. Pharmaceutical compositions according to the present invention are preferably administered parenterally, in particular intravenously. Preparations in the form of suspensions and solutions as well as easily reconstitutable dry preparations are suitable for all parenteral applications.

A pharmaceutical composition according to the invention can be produced by any method known in the state of the art.

The dosing of the components of a pharmaceutical composition according to the invention is subject to various factors, for example, the type of active pharmaceutical ingredient, the disease, the condition of the patient (mammal, preferably human) to which the pharmaceutical composition according to the invention is administered and how it is to be administered, e.g., parenterally, intravenously or by some other method. Those skilled in the art are familiar with such parameters and thus the determination of the doses is subject to the general technical knowledge of those skilled in the art.

Another subject matter of the invention relates to the use of a nanostructured delivery system or a pharmaceutical composition according to the invention for active and selective transport of the nanostructured delivery system or the pharmaceutical composition into a target tissue wherein the transport is triggered by the at least one polymethine dye as a targeting unit. The at least one polymethine dye especially preferably triggers uptake of the nanostructured delivery system or the pharmaceutical composition into the cells of the target tissue by means of at least one tissue-specific transporter. Accumulation of the nanostructured delivery system and/or its components in a target tissue can be detected in particular preferably by means of the fluorescent properties of the at least one polymethine dye. In addition to the at least one polymethine dye, at least one polymer, at least one lipid and/or at least one active pharmaceutical ingredient is/are to be understood as the components of the nanostructured delivery system (nanoparticles or liposomes).

Another subject matter of the invention relates to a nanostructured delivery system or a pharmaceutical composition according to the invention for use as a pharmaceutical drug.

Another subject matter of the invention relates to a nanostructured delivery system or a pharmaceutical composition according to the invention for use for the treatment of diseases and of the liver and/or kidneys, preferably infectious diseases involving damage to the liver and/or kidneys, for example, malaria and hepatitis C, liver failure, for example, drug-induced liver failure and fulminant liver failure, cirrhosis of the liver, for example, alcohol-induced cirrhosis of the liver, metabolic diseases of the liver, for example, Wilson's disease and Meulengracht disease, excretory dysfunctions of the liver, liver tumors, primary liver tumors, for example, hepatocellular carcinomas, angiosarcomas and hepatoblastomas, renal tumors, primary renal tumors, for example, clear-cell carcinoma, papillary carcinoma and chromophobic carcinoma, various types of nephritis, chronic and acute renal failure and diseases that trigger subsequent damage to the liver and/or kidneys, for example, sepsis.

The nanostructured delivery systems and targeting units according to the invention, in particular polymethine dyes, provide a unique possibility for combining diagnosis in one molecule with treatment. It is thus possible to make predictions about the efficacy of treatment by including the free targeting structure but to also monitor and control treatment with the same targeting structure on the nanoparticle or liposome. Due to the high flexibility of the targeting structure in the linker region, the targeting units may be chemically bound to a wide variety of lipids and polymers. Due to the chemical structure of the targeting unit, it is also very stable in contrast with biological targeting units (e.g., antibodies or peptides) and is accessible to chemical purification and analysis. Therefore a high reproducibility and controllability are possible in synthesis. Due to the property of the targeting unit as a ligand of tissue-specific transporters, these can be eliminated in vivo after desorption from the polymer so that the intracellular accumulation and toxicity are avoided. Due to current imaging developments in the field of multispectral optoacoustic tomography, the targeting unit can be detected directly. In addition, however, contrast media according to the invention for computer-assisted X-ray tomography or magnetic resonance tomography can also be enclosed in the nanoparticles or liposomes so that they can also be localized.

So far such a varied and cell-specific system, combining diagnosis and treatment via a dye as the targeting unit, which fluoresces in the red to infrared range and is then also eliminated very effectively by the liver and kidneys due to its selectivity for biotransporters, is unique.

The invention will also be illustrated as an example on the basis of the figures:

FIG. 1 shows an overview of the possible variations of a nanoparticle according to the invention and its influence on the physicochemical properties of nanoparticles themselves and on the biological consequences (Table 1).

FIG. 2 shows schematically the functionalization of the polymers according to the invention. A: Synthesis of the functionalized PLGA polymer by EDC coupling of the polymethine dye DY635 to the carboxylic acid terminal group of the PLGA to form DY635-PlGA-NP (or also referred to as DY635-PLGA; the two terms are used as synonyms in the present invention). B: SEC elugram of the functionalized PLGA polymers with UV and IR detectors. Synthesis and functionalization are also described in detail in Example 1.

FIG. 3 shows the design and production of nanoparticles according to the invention. The individual ultrasonic steps are characterized by gray needles (arrows). A detailed description can also be found in Example 2. A: Structure of the nanoparticles and their production by means of single emulsion technique. The hydrophobic polymer is shown in the dark gray with the hydrophobic active ingredient shown in the medium gray and the surfactant in water shown in the light gray. B: Structure of the nanoparticle and its production by means of the double emulsion technique. This shows the hydrophobic polymer in the dark gray and the hydrophobic active ingredient shown in white. The upper light gray layer is then again water with surfactant. C: Overview (cross sections) of the possible variations on a nanoparticle according to the invention and the influence thereof on the physicochemical properties of the nanoparticle itself and on the biological consequences (Table 1). The hydrophobic polymer or lipid is shown in black, and a possible active pharmaceutical ingredient, namely galactose and DY635 as the transporter for cell-specific uptake into hepatocytes, is/are shown in gray, where only the nanoparticles according to the invention retain their cell specificity.

Figure 4:
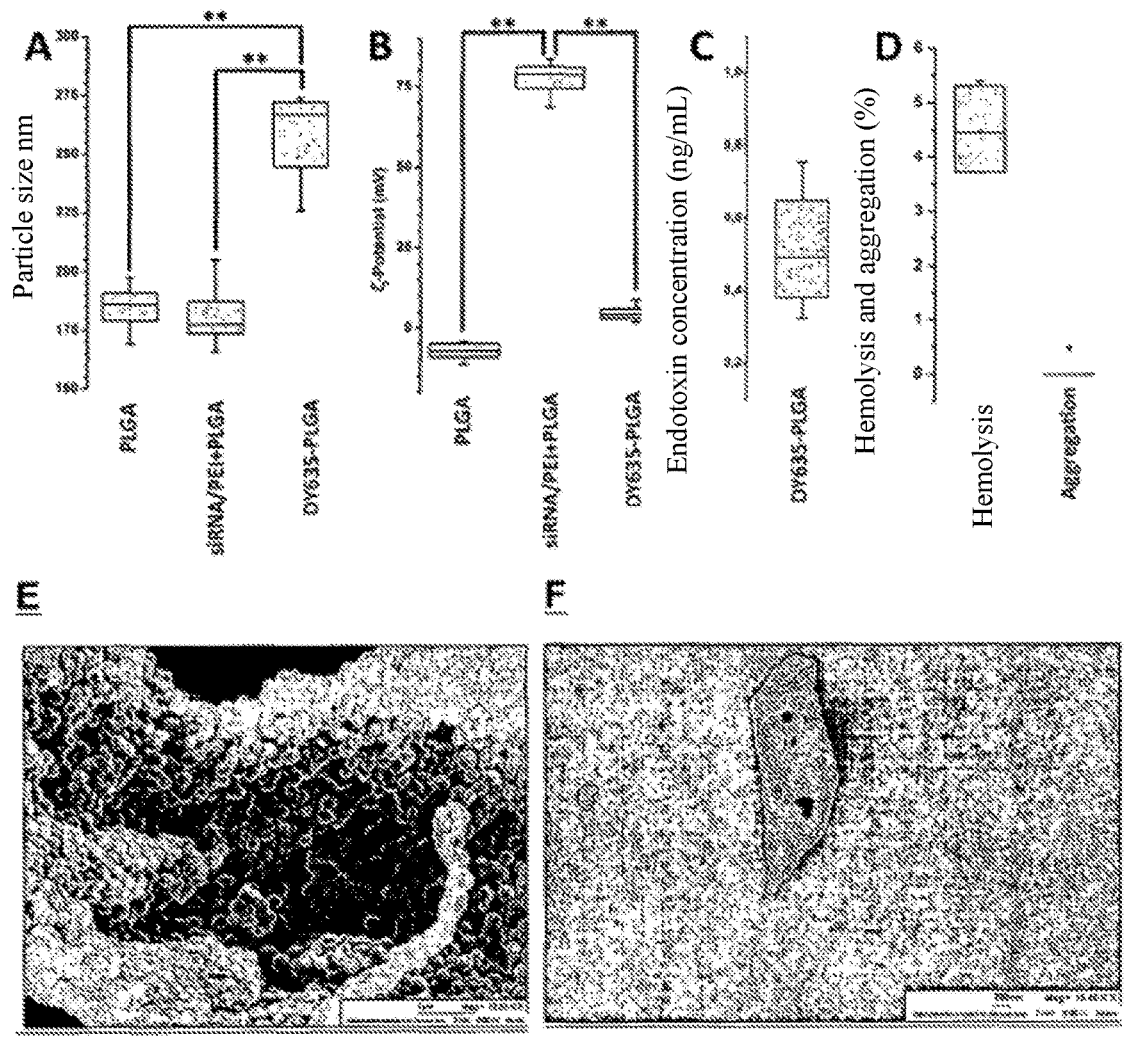

FIG. 4 shows the results of characterization of a selection of nanoparticles according to the invention. The box plots comprise the 0.25 to 0.75 quantile. The median is plotted as a horizontal bar, the mean as a cube. The whiskers each represent a highest and lowest value, respectively. A: The size of the PLGA nanoparticles does not differ from that of the siRNA/PEI-loaded PLGA nanoparticles (approximately 180 nm). However, the DY635-PLGA nanoparticles are significantly larger (approximately 260 nm). B: The zeta potential of PLGA nanoparticles is slightly negative. Due to the use of DY635-PLGA nanoparticles, the potential fluctuates into the weakly positive zeta potential (not significant). Due to the loading with the siRNA/PEI polyplexes (siRNA/PEI+PLGA nanoparticle), the zeta potential changes significantly and becomes strongly positive (+76 mV). C: For determining the amount of endotoxin, nanoparticle (NP) solutions in a concentration of 25 mg NP/mL, such as those also used in vivo, were investigated. The endotoxin load fluctuated between 0.4 mg/mL and 0.6 mg/mL in the samples. However, the value was always below the FDA limit value (2.5 ng/mL). D: NP solutions of 25 mg/mL are also used for the hemolysis and aggregation assays. Nanoparticles were used for the DY635-PLGA assay, such as those also used in the in vivo experiments. E and F: electron micrographs (SEM), E: unloaded, without targeting. F: loaded, with targeting. A further description of this can be found in Example 3.

Figure 5:
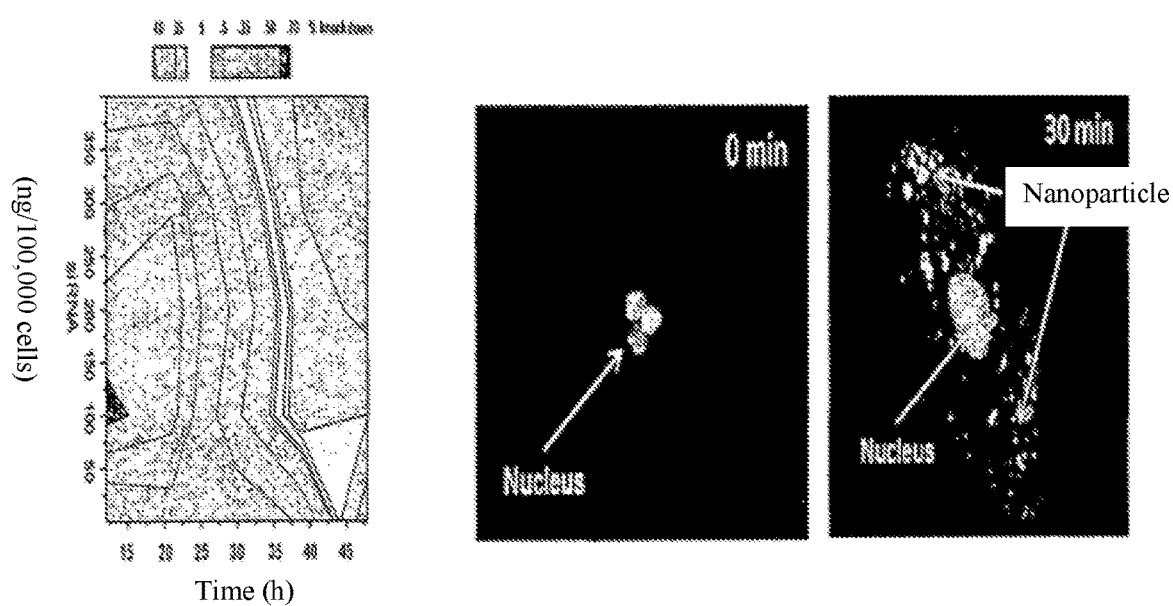

FIG. 5 shows the uptake kinetics and characterization of the RNAi into Hepa 1-6 cells in vitro. A: Diagram (heat map) describing the time- and concentration-dependent RNAi. The time is plotted in hours (h) on one axis against the siRNA concentration (ng/100,000 cells) on the other axis. The change in HMGCR expression in comparison with untreated controls is imaged in gray scale in percent (scale shown above the graph). For the points in the heat map, siRNA concentrations of 1, 5, 10, 25, 50, 100, 200 and 400 ng/100,000 cells were used and were tested after 12, 16, 24, 32, 40 or 48 hours. Three independent replicates were generated for each point in time. The result was then relativized against the HMGCR gene expression level of untreated Hepa 1-6 cells and normalized with the help of the HPRT gene expression. B: Uptake of the nanoparticles into Hepa 1-6 cells after 0 and 30 minutes (min). DY635 is visualized on LSM in the Cy5 channel. The cell nuclei were stained with DAPI after washing and fixing the cells. A further description of this process can be found in Example 4.

Figure 6:
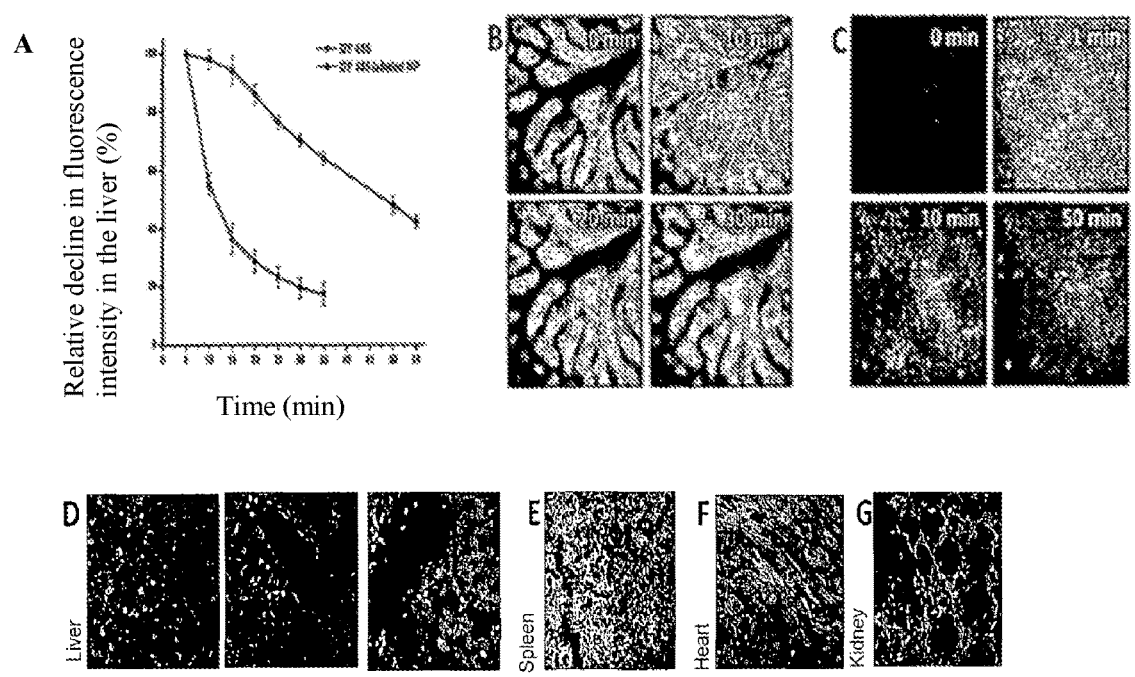

FIG. 6 shows the organ specificity and kinetics of a nanoparticle according to the invention in the liver, kidneys, spleen and heart. A: Comparison of the decay kinetics of DY635 versus DY635-PLGA-NP. Averages from 3 ROIs in the liver. Error bars show the SEM. B+C: Superimposing the images of Cy5 (DY635) channel (B light gray to white, C light gray) and DAPI (background) channel on the IVM at different points in time. D-G: 5 µm organ sections 10 minutes after DY635-PLGA-NP injection. DY635-PLGA-NP and/or DY635 (Cy5 channel, shown in green in the image) and the cell nuclei (DAPI-stained, shown in red in the image) are superimposed in the images. F, G: The stainings here are additionally superimposed on the liver structure (shown in blue in the image) visualized in phase contrast. A further description can be found in Example 5.

Figure 7:
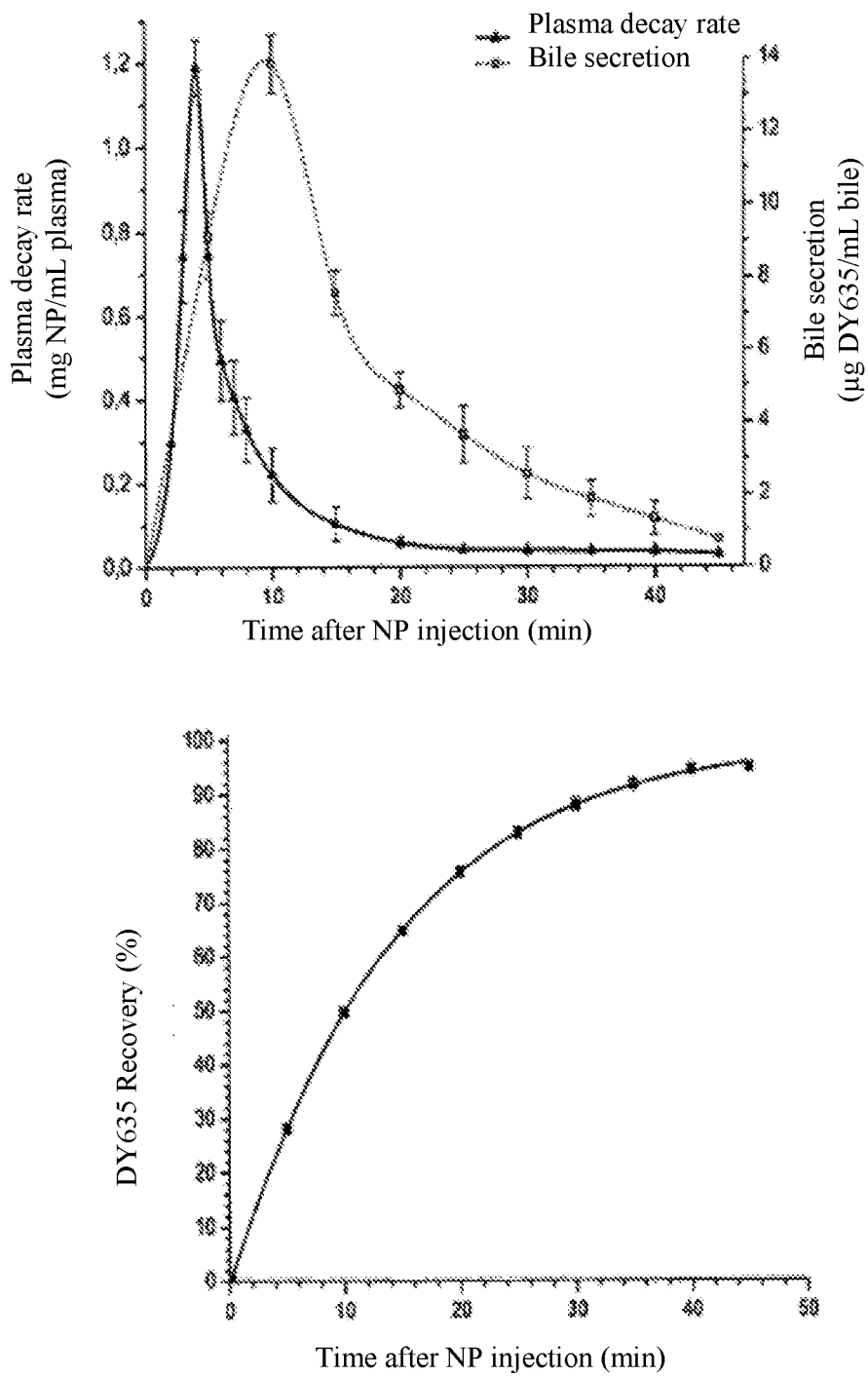

FIG. 7 shows the secretion route of a nanoparticle according to the invention. The secretion route of DY635-PLGA-NP: A: For calculating the plasma shrinkage rate, a standard curve is prepared in untreated plasma with DY635-PLGA nanoparticles. A standard series with DY635 in bile was used for the bile secretion. B: This shows the percentage DY635 "recovery" in the bile. The measurement points were computer-generated based on data from A. The curve was approximated by using OriginPro 8.5, QuickFit: exponential decay with offset approximated.

Figure 8:
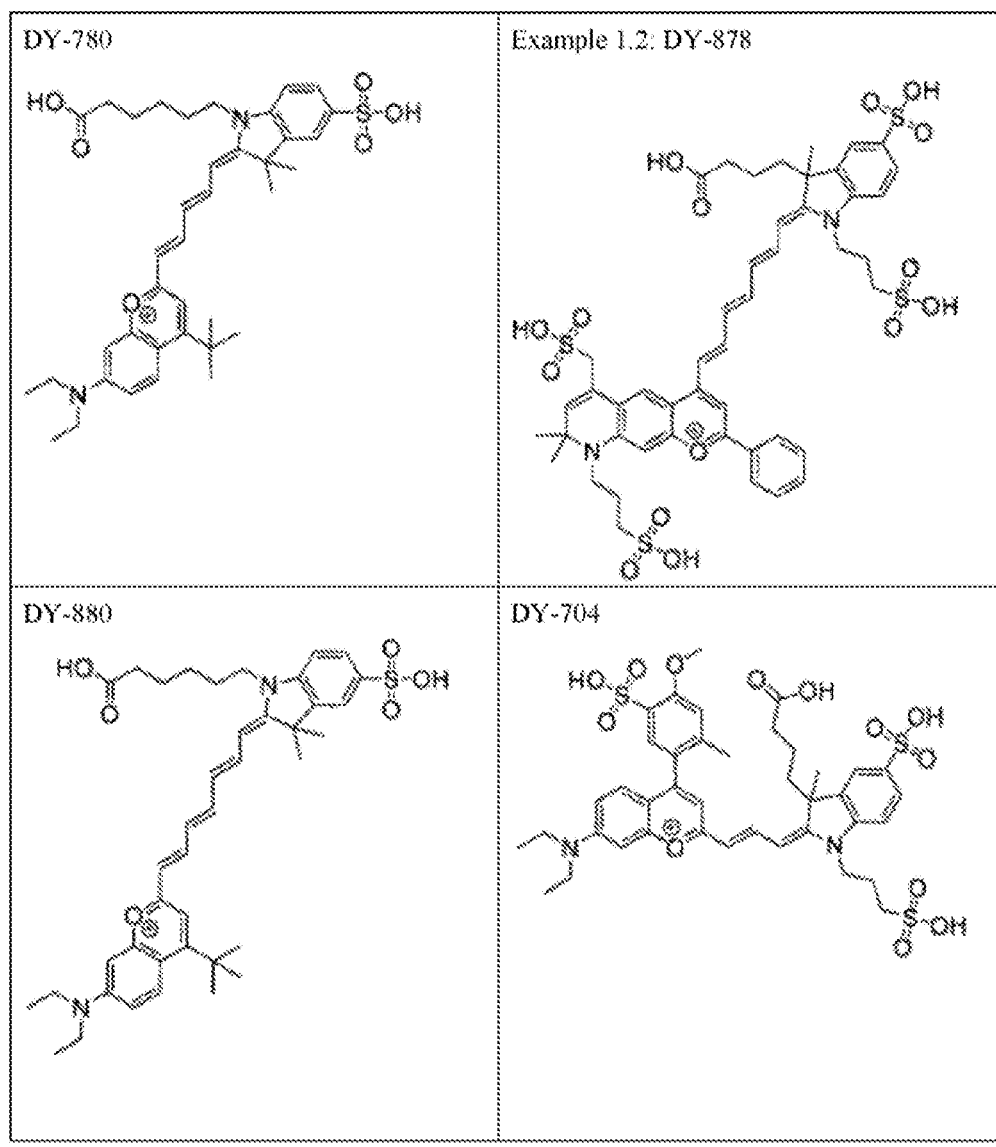
Figure 8:
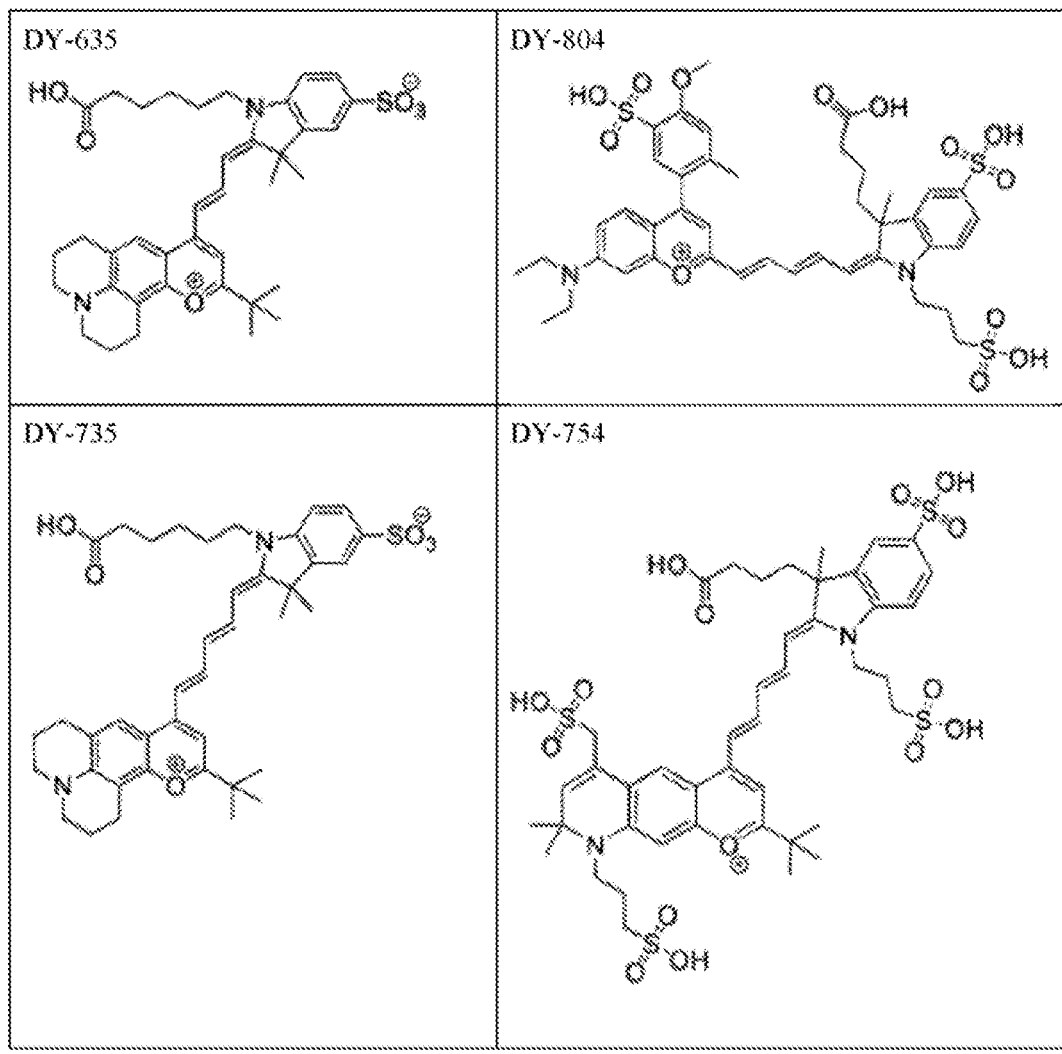
Figure 8:
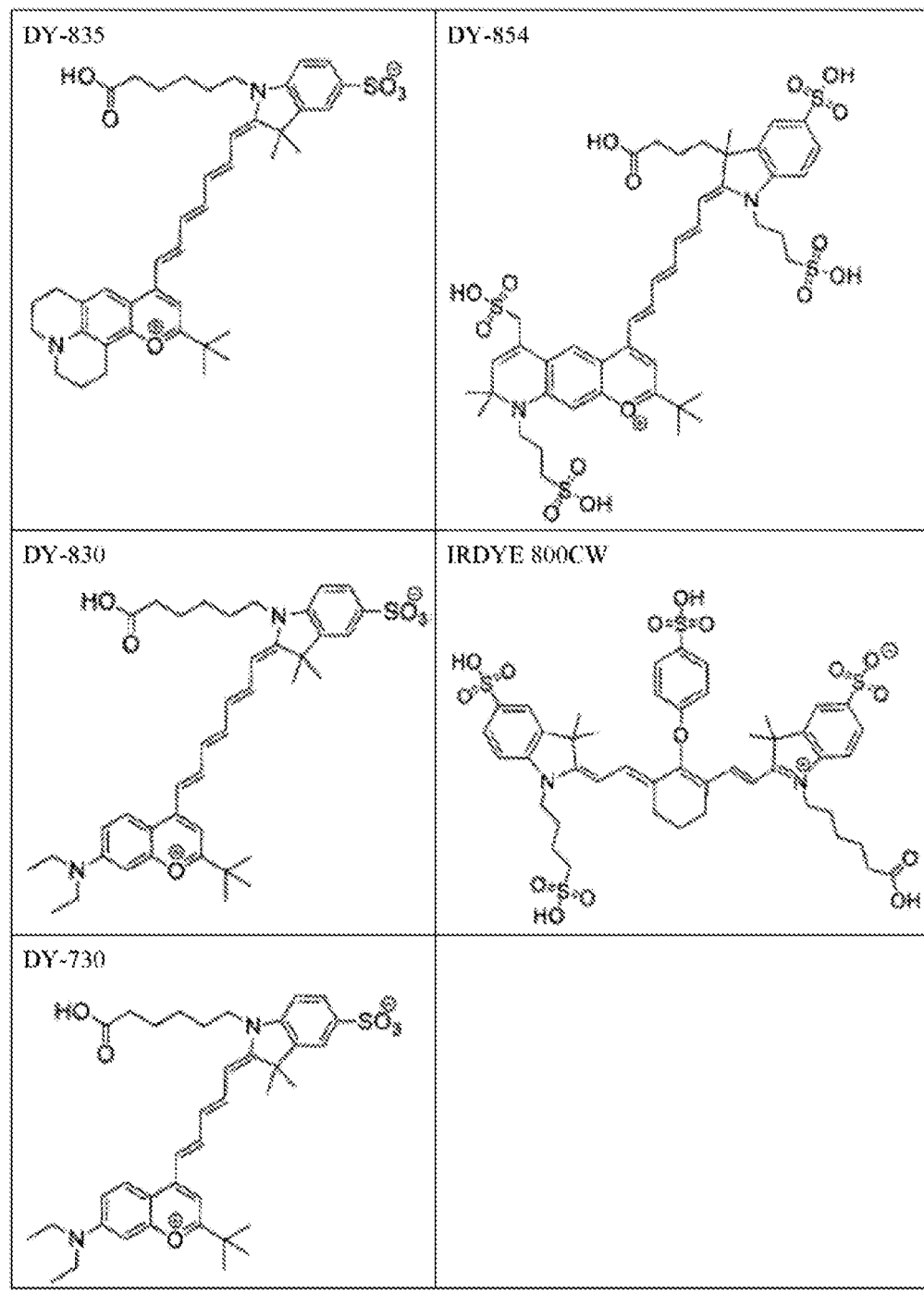
Figure 8:
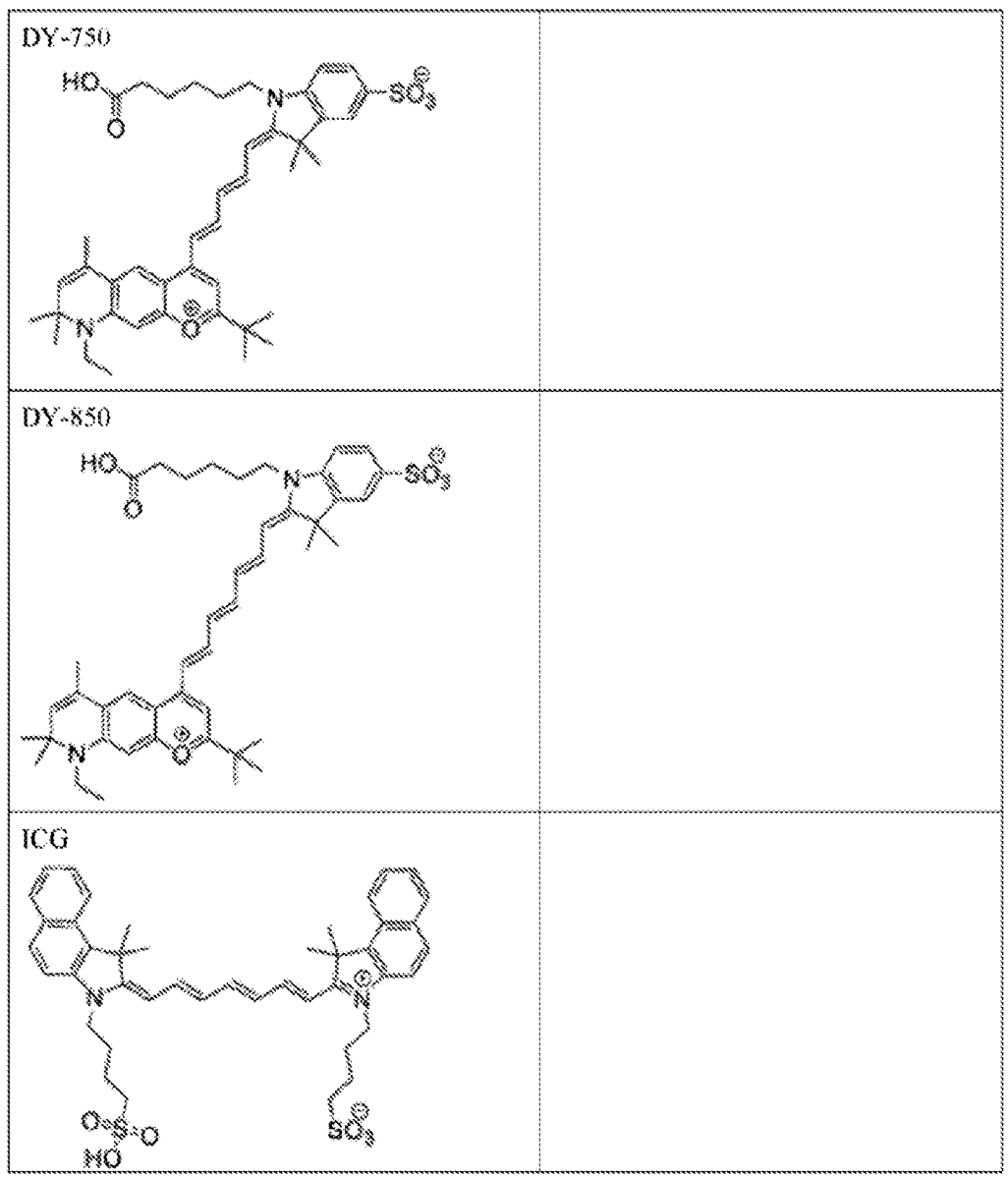

FIG. 8 shows targeting units according to the invention, namely polymethine dyes. FIG. 8 shows the general structure for a hepatocyte targeting unit and the general structure for a renal parenchyma cell targeting unit, specifying the linker to the polymer and/or lipid as well as examples of such hepatocyte targeting units and parenchyma cell targeting units (Table 2). The targeting units have a selectivity for one cell type (hepatocytes or renal parenchyma cells) and can transfer this cell selectivity to a nanoparticle or a liposome when they are bound to it by a chemical bond. The selectivity of the targeting unit occurs due to the interaction with influx transporters which are expressed by the target cells. The targeting units also have fluorescence properties in the red to infrared range. These fluorescence properties can be transferred to the nanostructured delivery system, more specifically to the nanoparticle or the liposome, so that not only can an accumulation of the dye be detected in the blood and in the tissue but also (if it is bonded to the nanoparticle and/or the liposome) accumulation of the nanoparticle and/or of the liposome can also be detected.

Figure 9:
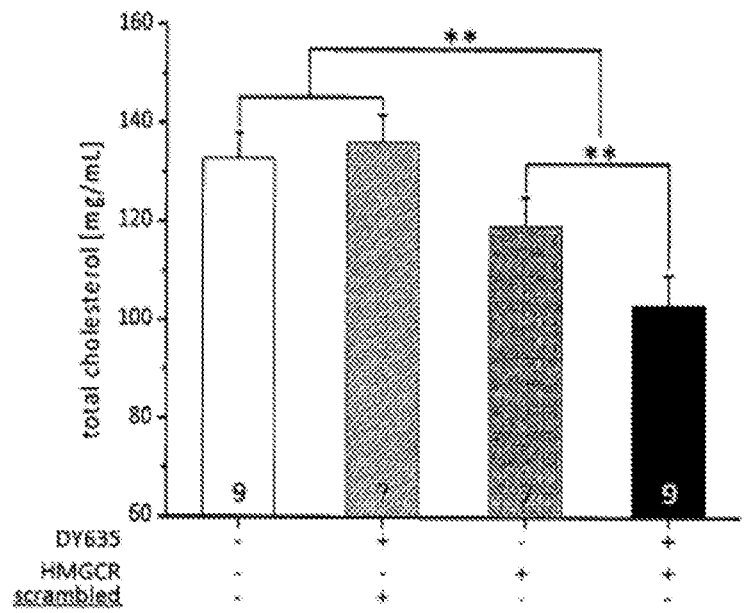
Figure 9:
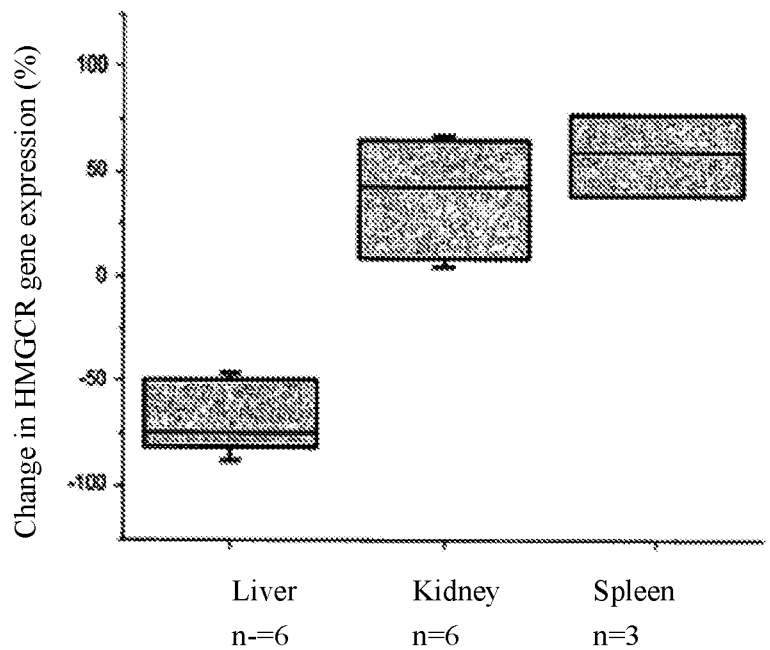

FIG. 9 shows the efficacy of the nanostructured delivery systems according to the invention in the transport of an active pharmaceutical ingredient. A: Plasma cholesterol levels after two injections of the nanostructured delivery systems which transport a siRNA toward the HMGCR and/or after two injections of a controlled substance. This figure shows a median bar plot, error bars describe the mean error of the standard deviation, the numbers in the bars describe the number of animals in each group, the significances were determined by a two-tailed U-test, ** significance level 0.01.

FIG. 9 A: These results show that it is possible through the approach described here to significantly lower the plasma cholesterol concentration. The organ-specific nanostructured delivery system shows the greatest effect. It is clear from FIG. 9 B that through the organ-specific nanostructured delivery system, an organ-specific and strong effect is achieved in hepatocytes. However, the nonspecific nanostructured delivery system does not show any specific or weaker down-regulation of the HMGCR.

Figure 10:
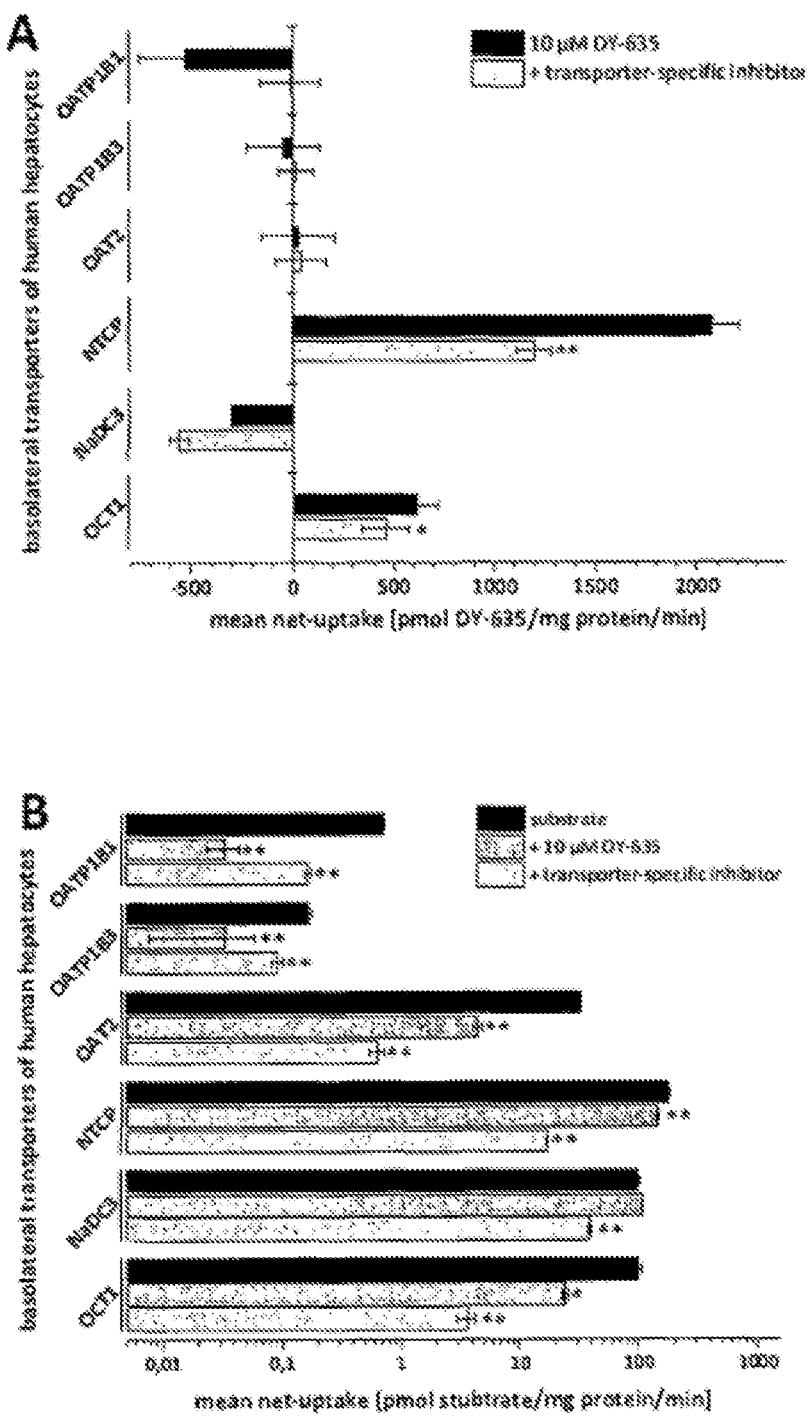

FIG. 10 shows the interaction according to the invention of a polymethine dye according to the invention as the targeting unit, DY-635, with a human basolateral hepatocyte transporter. FIGS. 10 A, B show bar plots of the mean value, with error bars describing the mean error of the standard deviation. All experiments here were performed six times each. The significances were determined by a bilateral U-test, **significance level 0.01, *significance level 0.01.

The invention is demonstrated below on the basis of examples, although it is not limited to them.

EXAMPLES

Example 1: Synthesis of Functionalized Polymers

The synthesized nanoparticles are based on the hydrophobic polymer poly(lactic-co-glycolic acid) (PLGA), which is biocompatible and biodegradable. This polymer can be bound covalently to an amine-functionalized dye on the basis of its active carboxylic acid group ("acid terminated") by means of coupling reagents such as EDC (1-ethyl-3-(3-dimethylaminopropyl)carbodiimide). The polymethine dye DY-635 was used here (see FIG. 2). Every 100th polymer chain was functionalized. The polymers were then separated from the free dye DY-635 by dialysis and purified by precipitation. The characterization was based on size exclusion chromatography (SEC), in which a UV/Vis detector and an RI (refractive index) detector were combined. Figure shows the graphic plot of the synthesis and an SEC elugram.

Example 2: Production of Nanoparticles

After functionalization of the polymers (Example 1), nanoparticles were produced by a single emulsion (A) and by a double emulsion (B) using high-frequency ultrasound, which promotes the formation of nanoscale particles with the help of surface-active substances (surfactants), i.e., polyvinyl alcohol (PVA) here. The hydrophobic polymers were therefore dissolved in ethyl acetate, a solvent that is not miscible with water (25 mg/mL). The surfactant used was 0.3% PVA (polyvinyl alcohol) in ultrapure water, where the total polymer concentration was 2.5 mg/mL. The polymer suspension in ethyl acetate was added to water with surfactant and nanoparticles were formed by using ultrasound (A). If hydrophilic substances were enclosed, then the hydrophilic substance was first dissolved in water and then added to the polymer in ethyl acetate and treated ultrasonically. Next, water with surfactant was added and nanoparticles were again formed by using ultrasound. FIG. 3 shows the results obtained by this emulsion technique.

The nanoparticles with a diameter of approximately 200 nm produced in this way were then stirred in a stream of air until the entire organic solvent (ethyl acetate) had evaporated and the particles were thus stable in water. To remove the excess surfactant, the nanoparticles were washed thoroughly with ultrapure water at least twice. This can be supported by vortexing and incubation in an ultrasonic bath. In conclusion the particles were lyophilized and their mass was determined.

Example 3: Characterization of the Nanoparticles

Nanoparticles of DY-635-conjugated PLGA (DY635-PLGA-NP) were produced with constant parameters and reproduced. The assays used for this are explained below:
Size: measurement of the size of the various nanostructured delivery systems dissolved in deionized water by dynamic light scatter (for example, Zetasizer (Malvern Instruments GmbH)) or by electron micrographs.
Shape: determination of shape by electron micrographs.
Charge: measurement of the various nanostructured delivery systems dissolved in deionized water using a Zetasizer (Malvern Instruments GmbH) by determining the electrophoretic signal (zeta potential, surface charge).
Endotoxins: endotoxin measurement by LAL chromogenic assay according to D. E. Guilfoyle, et al., *Evaluation of a chromogenic procedure for use with the Limulus lysate assay of bacterial endotoxins drug products*. J Parenter Sci Technol, 1985, 39(6): pp. 233-6.
Hemolysis: measurement of the hemoglobin concentration of erythrocytes which were incubated with the particles in physiological buffer for one hour. The measurable hemoglobin concentration in the supernatant increases when there is damage to the erythrocyte membrane.
Aggregation: Measurement of the absorption of erythrocytes incubated with the polymers in physiological buffer. Samples with cell aggregates show a lower absorption than homogeneously distributed unaggregated cells.

The results are shown in FIG. 4. A: size, B: charge, C: endotoxin load. For the size measurement, the dynamic light scatter was used and the charge was determined by means of the zeta potential. D: in addition it was shown that DY635-PLGA-NP does not have any lysine properties in blood and these do not lead to aggregation of erythrocytes. E and F: the particles have a round or spherical shape in the electron micrographs (SEM), both unloaded and without targeting (E) as well as loaded and with targeting (F).

Example 4: Triggering Drug-Associated Effects by RNAi and Uptake In Vitro ("Proof of Concept")

Procedure for FIG. 6 A: Hepa 1-6 cells were cultured under standard culture conditions (37° C., 5% $CO_2$, DMEM 4.5 g/L glucose, 10% heat-inactivated fetal bovine serum, 1% penicillin/streptomycin) in 6-well plates (100,000 cells per 9.6 $cm^2$). After 24 hours, various concentrations of the nanostructured delivery system which was prepared as described in Example 7 B were added to the wells and incubated for various periods (concentrations and incubation times can be seen in FIG. 5 A). After the incubation time, the cells were washed with Hank's Balanced Salt Solution (HBSS) and lysed with RLT buffer (Qiagen GmbH), to which 1% (3-mercaptoethanol was added. The mRNA was isolated from the lysate and analyzed in RT-qPCR. The values were then normalized on the hypoxanthin-guanine-phosphoribosyl transferase expression level and the HMGCR expression level (HMGCR: 3-hydroxy-3-methylglutaryl-coenzyme-A-reductase coenzyme or HMG-CoA) was compared with nontransfected Hepa 1-6 cells.

Procedure for FIG. 6 B: Hepa 1-6 cells were cultured under standard culture conditions on chamber slides (Nunc, Thermo Scientific GmbH) (5,000 cells/1.5 $cm^2$). After 24 hours, the cells were mixed with 100 µg/mL (final concentration) DY-635-modified nanostructured delivery system (produced as described in Example 7 B). After incubating for 30 minutes under standard culture conditions with the nanostructured delivery system, the cells were washed with HBSS and fixed with 5% formalin (pH 7) for 15 minutes. Then the microscope slides were washed with the cells and the cell nuclei were stained with DAPI. For analysis by laser scanning microscopy, the cells were moistened with VectaShield (Vector Labs, Inc.) and sealed with a cover glass. The nanostructured delivery system was detected by the modification with DY-635 at 633 nm (excitation) and the cell nuclei were visualized at 460 nm (excitation).

The results are shown in FIG. 5. A: The HMGCR gene expression could be downregulated by up to 70% by siRNA transfection in Hepa 1-6 cells. HMGCR (3-hydroxy-3-methylglutaryl-coenzyme-A-reductase or HMG-CoA) embodies the key enzyme of a central metabolism—the cholesterol biosynthesis. The downregulation of this metabolic gene demonstrated in this experiment shows the efficacy of the transport of the active ingredient according to the invention by the nanostructured delivery system. Furthermore, an elevated plasma cholesterol level is of central importance in the development of arteriosclerosis. The treatment method presented here using the nanostructured delivery systems according to the invention is an interesting alternative to traditional treatment with statins and in particular this is the first in the direction of gene transport for humans with a congenitally elevated cholesterol level (familial hypercholesterolemia). B: This shows that DY635-PLGA-NP is taken up by Hepa 1-6 cells (murine hepatocyte cell line) within 30 minutes. Such a rapid and intense uptake of a nanoparticle has not been described before in the prior art.

Example 5: In Vivo Targeting: Organ Specificity and Description of the Secretion Route Production of the nanostructured delivery system for this experiment was carried out as described in Example 2 (B). For the injection, the freeze-dried nanostructured delivery system was dissolved in a sterile 5% glucose solution (Glucosteril G5, Fresenius SE&Co KGaG) with the assistance of an orbital mixer and an ultrasonic bath.

Procedure (FIG. 6 A): Mice or rats were catheterized through a vein (jugular vein). Next the liver was prepared ex situ using an intravital microscope. Next DY-635 (13 pmol/g body weight (BW)) or the nanostructured delivery system carrying a DY-635 modification (6.5 µg/g BW) was injected venously and the specific fluorescence of DY-635 was measured at 633 nm in the liver over time and various Regions of Interest (ROIs) were quantified in the images recorded over time. FIG. 6 shows representative images of the measurement of DY-635 (FIG. 6 B) or DY-635-modified nanostructured delivery systems (FIG. 6 C). DY-635 or the DY-635-modified nanostructured delivery system was represented by the fluorescence of DY-635 at 633 nm. The liver structure was represented by the autofluorescence of NADH/NADH+ at 450 nm. To represent the organ specificity, male mice were injected with 6.5 µg of the DY-635-modified delivery system per g BW through a central venous catheter. The animal was euthanized painlessly 10 minutes after the injection and the organs were removed and cryoprepared for the histological workup. Next, 5-µm-thick sections of the organs were prepared with the cryotome and these were counterstained with DAPI. Then all the organs were examined at the same settings with regard to the DAPI-stained cell nuclei (at 430 nm) and with regard to the nanoparticle (at 633 nm).

The results are shown in FIG. 6. C: The DY635-PLGA-NP nanoparticles were taken up in the hepatocytes after just 1 minute (cobblestone-type signal-rich areas), imaging after 1 and 10 minutes (1 min, 10 min). After about 50 minutes (50 min), almost all the DY635 dye has been eliminated from the liver. Similar results were found with DY635. B: On the whole, the results are similar to those obtained in the earlier studies with the pure dye DY635. A: This shows the decay rate of DY635 in the liver. The altered decay rate of the DY635 intensity in the liver from DY635 and DY635-PLGA-NP shows that the DY635 dye is also still bound intracellularly to the PLGA polymer and is released and eliminated only after hydrolysis of the PLGA. D-G: This shows the organ specificities which were verified by means of various organ sections. After injection of DY635-PLGA-NP (green), the liver shows a marked accumulation. However, hardly any nanoparticles (spleen, heart) or no nanoparticles at all (kidneys) are visible in the spleen (E), the heart (F) and the kidneys (G).

Example 6: Secretion Route of the Nanoparticle DY635-PLGA

On the basis of this experiment, the plasma decay rate and the bile secretion of the DY635-PLGA nanoparticle and/or of the polymethine dye DY635 was investigated. This was done using male rats (strain: RccHan:WIST) with instrumentation (catheter in the jugular vein, carotid artery, common bile duct). Next, the substance to be tested is injected through the venous catheter. Then blood is taken from the arterial catheter at short intervals, and bile is taken from the catheter in the common bile duct. The blood is then processed further to plasma. The amount of DY635 was then measured by fluorimetry based on a calibration curve. DY635-PLGA-NP could be detected in the arterial blood at most after 4 minutes and was taken up almost completely into the organs up to 20 minutes after injection of DY635-PLGA-NP, i.e., within 15 minutes (min). There was a slight delay because as already described, DY635 must first be released from the nanoparticles and then DY635 is secreted into the bile (FIG. 6, illustration A). The (calculated) 95% recovery of DY635 in the bile also shows the high specificity of DY635-PLGA-NP for hepatocytes (FIG. 6, illustration B).

Example 7: Inclusion of Active Pharmaceutical Ingredients in Nanoparticles

After functionalization of the polymers or lipids with the targeting unit (Example 1), nanoparticles were produced by single emulsion (A) and double emulsion (B).
(A) Nanoparticles from a Single Emulsion If hydrophilic substances were to be included, the single emulsion technique was used. In this case the active ingredient is enclosed in a hydrophobic polymer core by hydrophobic interactions. The active ingredient was then dissolved together with the polymer in a suitable organic solvent. An organic solvent is suitable when it is neutral with respect to both the polymer and the active ingredient, i.e., it does not trigger any chemical changes therein and has no influence on their stability. Ethyl acetate was used in the present case. The mixture was overlayered with the hydrophilic solution. For stabilization of the nanoparticles and to increase the yield, a surfactant may be added to the hydrophilic solution in the case of double emulsion nanoparticles (cf. double emulsion nanoparticles). The two phases were combined by high-energy ultrasound emitted coaxially with an electrode immersed perpendicularly into the sample. This resulted in nanoparticles.
(B) Double Emulsion Nanoparticles For production, the hydrophobic polymers were dissolved in high concentration in a suitable solvent. An organic solvent is suitable when it is neutral with respect to both the polymer and the active ingredient, i.e., it does not alter them chemically and has no influence on their stability. Ethyl acetate was used in the present case. The concentration of the polymer depends on the size, hydrophilocity, solubility and stability of the polymer. Suitable concentrations here are between 2 and 50 mg/mL. The active ingredient was dissolved in ultrapure water in a suitable concentration. A suitable concentration of active ingredient depends on the chemical properties of the active ingredient and the capacitance of the nanoparticles. Following that, the shell polymer dissolved in the organic solvent was overlayered with the active ingredient dissolved in aqueous solution. The polymer and the organic solvent had to be present in the sample in an excess of at least tenfold. Particles that were hydrophobic on the outside were formed by bombarding with high-energy ultrasound coaxially with an electrode immerse in the sample. The active ingredient was thereby enclosed in a hydrophobic core due to interaction with hydrophilic groups of the nanoparticle in the interior. In the second step, a suitable surfactant was dissolved in ultrapure water in a suitable concentration. A surfactant concentration is adequate when it produces enough nanoparticles. The concentration depends on the ambient conditions and must be determined experimentally. It is usually between 0.01 and 5% (w/v). Then enough surfactant was added to the sample so that the concentration of polymer amount to only at least $\frac{1}{10}$ of the starting amount. Again two phases were formed and were mixed by high-frequency ultrasound emitted coaxially to an electrode immersed perpendicularly into the sample. By mixing the surface-active substances (surfactants), i.e., polyvinyl alcohol in the present case, the formation of water-soluble nanoscale particles was ensured.

For the sake of illustration, a batch is described, in which hydrophilic small interferin RNA (siRNA) complexed with polyethyleneimine (PEI) was enclosed in PLGA nanoparticles. The PLGA was first modified with DY-635, so that one out of every 200 chains would carry a dye molecule:
(1) 2.4 µL PEI (1 mg/mL) was mixed with 2 µL siRNA (1 µg/µL) and mixed with 45.6 µL ultrapure water. The mixture is referred to below as a polyplex because the anionic siRNA and the cationic PEI interact with one another and a PEI binds and stabilizes the siRNA in a tight mesh network.

(2) 325 mg DY-635-conjugated PLGA was dissolved in a total of 12.35 µL ethyl acetate.

(3) 90 µL polymer solution from (2) was mixed with 50 µL polyplexes from (1) with high-frequency ultrasound (emitted as described above).

(4) 1 mL PVA 0.3 wt % in ultrapure water was added to the mixture, which was then exposed to ultrasound.

(5) The resulting nanoparticles were purified and freeze-dried.

Purification (for (A) and (B))

The nanoparticles produced in this way had a diameter which was a function of the size and material of the vessels, the intensity of the ultrasound and the substance concentration and had a size of 120 to 220 nm. Under stable conditions, after producing the nanoparticles, the solvent was removed. To remove excess surfactant, the nanoparticles were washed several times (at least twice) by centrifuging, removing the supernatant and resuspending the nanoparticles in sterile ultrapure water. Then the particles were lyophilized and their mass was determined.

Example 8: Inclusion of Active Pharmaceutical Ingredients in Liposomes

After functionalization of the polymers or lipids with the targeting unit (Example 1), liposomes were produced as follows:

1. Production of a 50 mM lipid solution from for example, 1:1 DOPC:DSPC (1,2-dioleolyl-sn-glycero-3-phosphocholine:1,2-distearol-sn-glycero-3-phospholine)+30% cholesterol+5% N-dod-DOPE in chloroform/methanol (2:1 vol/vol). Before being used, the DOPC can be modified with a polymethine dye.
2. Evaporation of the chloroform/methanol solvent (approximately 30 min, 90 rpm) in a rotary evaporator.
3. The lipids were then dissolved in 1 mL 7:3 vol/vol mixed DMSO:EtOH.
4. Next the hydrophilic dextran as the active ingredient was dissolved in a suitable buffer, namely PBS (phosphate buffered solution) to yield a concentration of 1 mg/mL.
5. 0.3 mL of the lipid solution was then added by drops to the dextran solution was then kept in motion at 750 rpm on a magnetic agitator while the dropwise addition was underway.
6. The liposomes were then separated in a miniextruder.
7. Next the liposome solution was aliquoted in 1-mL containers and alternately frozen in liquid nitrogen and then thawed in hot water 10 times.
8. Next the liposomes were separated 10 times in the extruder.
9. Then the liposomes were dialyzed in a prepared dialysis cassette (MWCO=20 kDa) against PBS for 16 hours.
10. Next the liposomes were freeze-dried, stored or used.

Example 9: Influencing Cholesterol Biosynthesis by the Organ-Specific Transport of an siRNA Against HMG-CoA Reductase (HMGCR) in DY-635-Modified Nanostructured Delivery Systems Male FVB/NRj mice (10 weeks old) were treated twice at intervals of 24 hours with the DY-635-modified nanostructured delivery system by i.v. injection by injecting 6.5 µg of the nanostructured delivery system per kg body weight. The delivery system was produced as described in Example 7 (B), wherein PLGA-modified with 108 µg PEI was enclosed in 3 mg DY-635 for production of 3 µg siRNA against HMGCR or 3 µg scrambled siRNA (siRNA without effect). The animals were euthanized painlessly 16 hours after the second injection and both blood and organs were removed for analysis. The blood was removed in lithium heparin monovettes and processed to plasma. To determine the efficacy of the treatment, the total cholesterol was determined in the plasma, and for the specificity, the change in gene expression in various organs was determined in qPCR. These values were compared with the cholesterol and the HMGCR expression level of healthy FVB/NRj mice (10 weeks old) and control groups. The control groups had the following composition:

treatment with a DY-635-modified and therefore hepatocyte-specific nanostructured delivery system and an ineffective scrambled siRNA;

treatment with a nanostructured delivery system that did not contain any DY-635 modification but otherwise did not differ from the therapeutic construct;

the animals received only the 5% glucose solution.

Example 10: Detecting the Interaction of DY-635 with Hepatocytic Transporters

HEK-293T cells were transfected with human tissue-specific hepatocytic transporters. Then the uptake of the polymethine dye DY-635 as a targeting unit into these tissue-specific transporters was investigated for FIG. 10 A. To do so, the cells were sown onto 96 well plates, incubated for 24 hours under standard conditions, then incubated 5 minutes with DY-635 (final concentration in the well: 10 µmol/L) after changing the medium. Next the cells were lysed and the lysates were measured by fluorimetry. The quantity of DY-635 taken up was quantified by a DY-635 standard curve using the respective transporters which had been specifically inhibited for the controls (inhibitors and the final concentrations used are shown in the following Table 3). In this experiment, it was found that DY-635 is a substrate for NTCP. The uptake by OCT1 can be evaluated as negligible. In FIG. 10 B the question of whether DY-635 binds as an inhibitor to the basolateral hepatocytic transporters was investigated. For this purpose, the HEK-293T cells transfected with the tissue-specific transporters were sown and incubated as described above. After 24 hours the cells were incubated for 5 minutes with either a radioactively labeled transporter-specific substrate or with the radioactive-specific substrate with a specific inhibitor or with DY-635 (10 µmol/L final concentration) (the substrates and their concentrations are shown in Table 3 below). The cells were then washed and lysed in the well. To quantify the uptake, the radioactive radiation of the substrates was used. It was found here that DY-635 is a strong indicator for OATP1B1 and OATP1B3. OAT2 and OCT1 are also inhibited by DY-635. This illustrates the strong interaction of DY-635 with the tissue-specific hepatocytic transporters. It can be concluded that by exposure of DY-635 to the surface of a nanostructured transporter system, immobilization on the cell surface of the hepatocyte occurs, resulting in subsequent endocytosis of the nanoparticle.

TABLE 3

| Human hepatocytic transporter | Radioactively labeled transporter-specific substrate/concentration | Transporter-specific inhibitor/concentration |
|---|---|---|
| OATP1B1 | [$^3$H]Estradiol/30 nM | Rifampicin/5 μM |
| OATP1B3 | [$^3$H]Sulfobromophthalein sp/50 nm | Rifampicin/5 μM |
| OAT2 | [$^3$H]cGMP/10 nM | Indomethacine/100 μM |
| NTCP | [$^3$H]Estradiol/30 nM | Cyclosporin A/50 μM |
| NaDC3 | [$^{13}$C]Succinate/10 μM | Succinate/100 μM |
| OCT1 | [$^3$H]1-Methyl-4-phenylpyridinium | Decynium22/40 μM |

The invention claimed is:

1. A method for targeted transport into a target tissue, comprising contacting a target tissue with a nanostructured delivery system comprising at least one polymer and/or at least one lipid and at least one polymethine dye,
wherein the at least polymethine dye triggers transport of the nanostructured delivery system into the target tissue, and
wherein the at least one polymethine dye is a symmetrical or asymmetrical polymethine of the general structure I, II, or III:

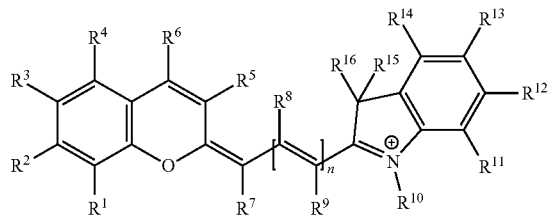

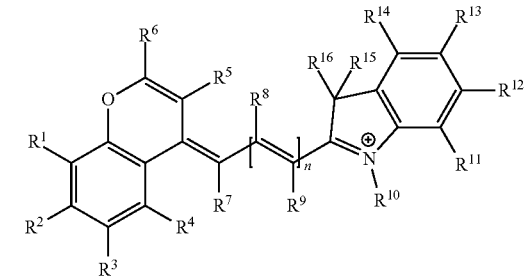

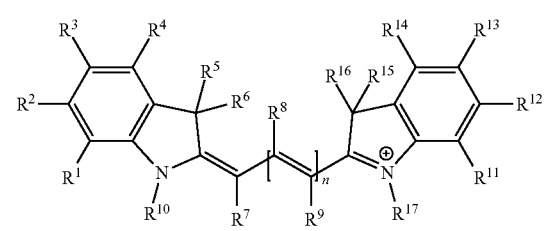

where
a. n stands for the numerical values 0, 1, 2, 3, 4, 5, 6, 7, 8, 9 or 10;
b. $R^1$-$R^{17}$ may be the same or different and may be hydrogen, one or more alkyl, tert-alkyl, cycloalkyl, olefinic structures, aryl, carboxyaryl, dicarboxyaryl, heteroaryl or heterocycloaliphatic radicals, alkyloxy, alkylmercapto, arlyoxy, arylmercapto, heteroaryloxy, heteroarylmercapto groups, hydroxyl, nitro or cyano group, an alkyl-substituted or cyclic amine function and/or two ortho-position radicals, together may form an additional aromatic, heteroaromatic, aliphatic or heteroaliphatic ring; wherein alkyl or cycloalkyl radicals comprising fused ring systems between $R^3$ and $R^4$ or $R^{13}$ and $R^{14}$ form only one ring fusion;
c. at least one of the $R^1$-$R^{17}$ substituents has a solubilizing and/or ionizable or ionized substituent, which determines the hydrophilic properties of these polymethine dyes, wherein this substituent may also be bound to the polymethine dye by a spacer group;
d. at least one of the $R^1$-$R^{17}$ substituents has a reactive group (linker), wherein this substituent may also be bound to the polymethine dye by a spacer group; and
e. an aromatic, heteroaromatic, aliphatic or heteroaliphatic spacer group is bound to one of the $R^1$-$R^{17}$ substituents;
f. the $R^8$ and $R^9$ substituents with corresponding n=2, 3, 4 or 5, may also be present 2×, 3×, 4× or 5×, and these may be the same or different.

2. The method according to claim 1, wherein the at least one polymethine dye triggers the uptake of the nanostructured delivery system into the cells of the target tissue.

3. The method according to claim 1, wherein the nanostructured delivery system additionally comprises at least one active pharmaceutical ingredient.

4. The method according to claim 1, wherein the at least one polymethine dye is selected from the group consisting of DY635, DY-680, DY-780, DY-880, DY-735, DY-835, DY-830, DY-730, DY-750, DY-850, DY-778, DY-878, DY-704, DY-804, DY-754, DY-854, DY-700, DY-800, ICG and DY-IRDYE 800CW.

5. The method according to claim 1, wherein the at least one polymer is selected from the group consisting of polyesters, poly(meth)acrylates, polystyrene derivatives, polyamides, polyurethanes, polyacrylonitriles, olytetrafluoroethylenes, silicones, polyethylene glycols, polyethylene oxides and polyoxazolines and their copolymers or the at least one lipid is selected from the group consisting of saturated and unsaturated fatty acids.

6. The method according to claim 2, wherein the at least one tissue-specific transporter is selected from the group consisting of OATP1B1, OATP-C, OATP2, LST-1, OATP1B3, OATP8, OATP2B1, OATP1A2, NaDC3, SDCT, NTCP, OCT1, OCT3, OAT2, OAT1, OAT3, PGT, OCT2, OATP4A1, and OATP4C1.

7. The method according to claim 3, wherein the at least one active pharmaceutical ingredient is selected from the group consisting of inductors, contrast media, nucleic acids, proteins.

8. The method of claim 1, wherein accumulation of the nanostructured delivery system and/or its components in the target tissue is detectable by means of the fluorescence properties of the at least one polymethine dye.

9. The method according to claim 3, wherein the target tissue is liver and/or kidneys of a subject with a disease of the liver and/or kidneys, and the method serves to treat the disease of the liver and/or kidneys.

10. The method according to claim 9, wherein the disease is selected from the group consisting of infectious diseases involving damage to the liver and/or kidneys, liver failure, cirrhosis of the liver, metabolic diseases of the liver, excretory dysfunctions of the liver, liver tumors, primary liver tumors, kidney tumors, primary kidney tumors, nephritis conditions, chronic and acute renal failure and diseases that cause subsequent damage to the liver and/or kidneys.

11. The method according to claim 1, wherein the solubilizing and/or ionizable or ionized substituent is selected from the group consisting of $SO_3^-$, ($-SO_3H$), $PO_3^2$, COOH, OH or $NR_3^+$, cyclodextrins, and sugar.

12. The method according to claim 1, wherein the reactive group is selected from the group consisting of isocyanates, isothiocyanates, hydrazines, amines, mono- and dichloro- or mono- and dibromotriazines, aziridines, epoxies, sulfonyl halides, acid halides, carboxylic anhydrides, N-hydroxysuccinimide esters, imido esters, carboxylic acids, glyoxal, aldehyde, maleimide or iodacetamide and phosphoramidite derivatives, azides, alkynes or olefins.

13. The method according to claim 1, wherein the aromatic, heteroaromatic, aliphatic, or heteroaliphatic spacer group consists of structural elements of formula $[(CH_2)_a-Y-(CH_2)_b]_c$ or $[(C_6H_4)_a-Y-(C_6H_4)_b]$, where Y may be the same or different and comprises $CR_2-$, $O-$, $S-$, $SO_2$, $SO_2NH-$, $NR-$, $COO-$ or CONR functions; a and b may be the same or different and have numerical values of 0-18, and wherein c has a numerical value of 0-18.

14. The method according to claim 5, wherein the polymer comprises random, gradient, alternating, block, graft or star copolymers.

15. The method according to claim 5, wherein the saturated and unsaturated fatty acids are selected from the group consisting of cholesterol, palm ethyl acid, phospholipids, sphingolipids, and glycolipids.

* * * * *